US011495915B2

(12) United States Patent
Suzuki et al.

(10) Patent No.: US 11,495,915 B2
(45) Date of Patent: Nov. 8, 2022

(54) CONNECTOR APPARATUS AND ENDOSCOPE APPARATUS PROVIDED WITH CONNECTOR APPARATUS

(71) Applicant: OLYMPUS CORPORATION, Tokyo (JP)

(72) Inventors: Ryusuke Suzuki, Hachioji (JP); Minoru Sato, Hino (JP); So Matsuka, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 308 days.

(21) Appl. No.: 16/853,908

(22) Filed: Apr. 21, 2020

(65) Prior Publication Data

US 2020/0245849 A1    Aug. 6, 2020

Related U.S. Application Data

(63) Continuation of application No. PCT/JP2018/026520, filed on Jul. 13, 2018.

(30) Foreign Application Priority Data

Oct. 26, 2017  (JP) .............................. JP2017-206977

(51) Int. Cl.
*H01R 13/641* (2006.01)
*A61B 1/00* (2006.01)
(Continued)

(52) U.S. Cl.
CPC ....... *H01R 13/641* (2013.01); *A61B 1/00124* (2013.01); *G02B 23/2476* (2013.01); *H01R 13/6683* (2013.01)

(58) Field of Classification Search
CPC .............. H01R 13/641; H01R 13/6683; A61B 1/00124; G02B 23/2476
See application file for complete search history.

(56) References Cited

U.S. PATENT DOCUMENTS

| 9,583,860 B1* | 2/2017 | DeWitte ............... H01R 13/436 |
| 2011/0159723 A1 | 6/2011 | Fukushima |
| 2017/0003459 A1* | 1/2017 | Takeuchi ............ G02B 6/3821 |

FOREIGN PATENT DOCUMENTS

| GB | 2540972 A * | 2/2017 | .......... G01R 31/045 |
| JP | H1-93912 U | 6/1989 | |

(Continued)

OTHER PUBLICATIONS

International Search Report dated Sep. 18, 2018 issued in PCT/JP2018/026520.

*Primary Examiner* — Tho D Ta
(74) *Attorney, Agent, or Firm* — Scully, Scott, Murphy & Presser, P.C.

(57) ABSTRACT

A connector apparatus of the present invention includes a receptacle into which a plug is inserted, a moving member configured to move in conjunction with insertion of the plug, and a sensor provided below the receptacle and configured to detect presence or absence of the plug in the receptacle, in which the moving member includes a first portion extending downward, a second portion, one end of which is connected to the first portion and another end of which is located above the one end, and a third portion, one end of which is connected to the second portion and configured to move in conjunction with the insertion of the plug to thereby switch between a first state in which the plug is disposed in a predetermined region and a second state in which the plug is not disposed in the predetermined region.

17 Claims, 12 Drawing Sheets

(51) Int. Cl.
G02B 23/24 (2006.01)
H01R 13/66 (2006.01)

(56) References Cited

FOREIGN PATENT DOCUMENTS

| | | | |
|---|---|---|---|
| JP | 2001-161642 A | 6/2001 | |
| JP | 2005-056630 A | 3/2005 | |
| JP | 2008-93113 A | 4/2008 | |
| JP | 2011-91027 A | 5/2011 | |
| JP | 2016-154401 A | 8/2016 | |
| KR | 20130142388 A * | 12/2013 | |
| WO | WO-2012065594 A2 * | 5/2012 | ............. B60L 1/003 |

* cited by examiner

CONNECTOR APPARATUS AND ENDOSCOPE APPARATUS PROVIDED WITH CONNECTOR APPARATUS

CROSS REFERENCE TO RELATED APPLICATION

This application is a continuation application of PCT/JP2018/026520 filed on Jul. 13, 2018 and claims benefit of Japanese Application No. 2017-206977 filed in Japan on Oct. 26, 2017, the entire contents of which are incorporated herein by this reference.

BACKGROUND OF INVENTION

1. Field of the Invention

The present invention relates to a connector apparatus including a plug and a receptacle or the like configured to relay a connection between an endoscope and an external device using an electric signal line, an optical fiber cable or the like, and an endoscope apparatus provided with the connector apparatus.

2. Description of the Related Art

Conventionally, endoscopes provided with an elongated tube-shaped insertion portion have been widely used, for example, in a medical field, an industrial field and the like. Among such endoscopes, medical endoscopes used in the medical field are configured to observe an organ or the like with an insertion portion inserted into, for example, a body cavity of a living body or apply various types of treatment to the organ or the like as required using a treatment instrument inserted into a treatment instrument insertion channel provided in the endoscope. Industrial endoscopes used in the industrial field are configured to observe and inspect a state of a scar or corrosion in an apparatus such as a jet engine or factory pipes or machine equipment by inserting an insertion portion into the apparatus or the machine equipment or the like.

In general, an example of such an endoscope is a so-called electronic endoscope provided with an image pickup unit including a solid image pickup device such as a charge coupled device (CCD image sensor) at a distal end of an endoscope insertion portion. A signal outputted from an image pickup device of the image pickup unit of the electronic endoscope is turned into a video signal via an image processing apparatus as an external device configured separately from the endoscope. The video signal is outputted to a display apparatus and displayed as an observation image (image of an object to be observed such as an organ in the body cavity) visually recognizable using a display section of the display apparatus.

At this time, the endoscope and the external device (image processing apparatus) are connected using an electric signal line, an optical fiber cable or the like. With a connector apparatus composed of a plug and a receptacle interposed on the wiring, the endoscope and the external device (image processing apparatus) are made freely attachable/detachable to/from each other.

Thus, the apparatus constituted by connecting the endoscope, the external device (image processing apparatus) and the display apparatus as a whole is generically called an "endoscope apparatus."

Connector apparatuses used for conventional endoscope apparatuses are configured such that by fitting a plug provided at an end part of a wiring cable such as an electric signal line or an optical fiber cable into a receptacle set on a casing surface of the device, the wiring cable may be easily connected to an electric circuit or the like in the device or may be easily removed.

In normal cases, when a medical endoscope apparatus is used, various kinds of liquids may often be used, and, for example, a liquid carelessly spilled during operation of the endoscope apparatus may be introduced into the endoscope or the external device, and therefore measures need to be devised to prevent such intrusion of the liquid into the endoscope or the external device.

Especially, the connector apparatus of the endoscope apparatus is provided with electric parts for maintaining an electrical connection and an electric substrate mounted with the electric parts or the like, and liquids or the like should not be attached to the electric parts or the like as much as possible.

Therefore, a connector apparatus of a conventional endoscope apparatus provided with a lid member or an opening/closing type cover member for protecting a receptacle opening is disclosed, for example, in Japanese Patent Application Laid-Open Publication No. 2008-93113 or the like.

Furthermore, a connector apparatus of a conventional endoscope apparatus in various forms designed to avoid an intruding liquid or the like from reaching an electric substrate or the like is disclosed, for example, in Japanese Patent Application Laid-Open Publication No. 2016-154401.

The configuration disclosed in above Japanese Patent Application Laid-Open Publication No. 2016-154401 or the like is such that a liquid flowing downward along a cable member provided above is led to another eaves member via another member (collar member) provided at a midway position of the cable member to thereby prevent the liquid or the like from flowing toward the connector apparatus.

Furthermore, in the case of the connector apparatus of the conventional endoscope apparatus, electric parts and an electric substrate or the like are arranged an above part of the receptacle opening, and various configurations are considered to prevent a spilled liquid from infiltrating or depositing onto the electric parts and the electric substrate or the like.

SUMMARY OF THE INVENTION

A connector apparatus according to an aspect of the present invention includes a receptacle into which a plug provided at a terminal end of a cable is inserted, the receptacle being provided in a device to which the plug is connected, a moving member in contact with the receptacle and configured to move in conjunction with insertion of the plug into the receptacle, and a sensor provided below the receptacle and configured to detect presence or absence of the plug in a predetermined region in the receptacle, in which the moving member includes a first portion extending downward from a vicinity of a contact region with the receptacle, a second portion, one end of the second portion is connected to the first portion and another end of the second portion is located above the one end, and a third portion, one end of the third portion is connected to the second portion and configured to move in conjunction with the insertion of the plug into the receptacle to thereby switch between a first state in which the plug is disposed in the predetermined region and a second state in which the plug is not disposed in the predetermined region according to the detection by the sensor.

An endoscope apparatus according to another aspect of the present invention includes a receptacle into which a plug provided at a terminal end of a cable extending from an endoscope is inserted, the receptacle being provided in a casing device to which the plug is connected, a moving member in contact with the receptacle and configured to move in conjunction with insertion of the plug into the receptacle, and a sensor provided below the receptacle and configured to detect presence or absence of the plug in a predetermined region in the receptacle, in which the moving member includes a first portion extending downward from a vicinity of a contact region with the receptacle, a second portion, one end of the second portion is connected to the first portion and another end of the second portion is located above the one end, and a third portion, one end of the third portion is connected to the second portion and another end of the third portion is formed to extend downward, and configured to move in conjunction with the insertion of the plug into the receptacle to thereby switch between a first state in which the plug is disposed in the predetermined region and a second state in which the plug is not disposed in the predetermined region according to the detection by the sensor.

DETAILED DESCRIPTION OF THE PREFERRED EMBODIMENTS

Hereinafter, the present invention will be described according to embodiments illustrated in the accompanying drawings. Each drawing used in the following description is intended for schematic illustration, and respective components may be shown in different dimensional relationships and scales among respective members so that the respective components are shown in sizes to make them recognizable on the drawings. Therefore, the present invention is not limited to only the illustrated forms with regard to quantities of the components, shapes of the components, size ratios among the components and relative positional relationships among the components described in the respective drawings.

[First Embodiment]

A connector apparatus according to a first embodiment of the present invention includes a plug and a receptacle or the like in an endoscope apparatus, configured to detachably relay connections using an electric signal line, an optical fiber cable or the like between an endoscope and an external device.

Figure 1:
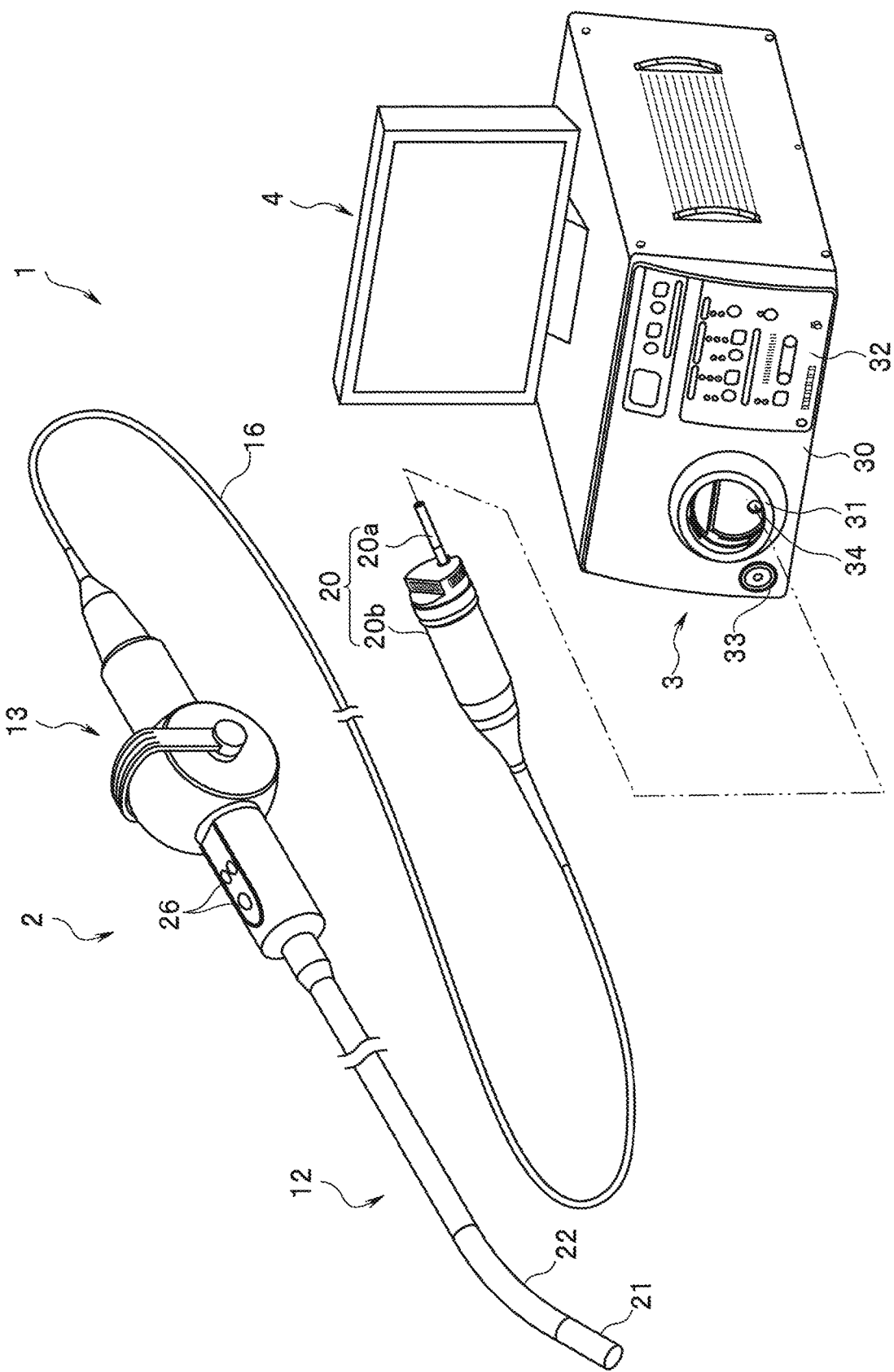
FIG. 1 is an external perspective view illustrating a schematic configuration of an endoscope apparatus provided with a connector apparatus according to a first embodiment of the present invention.

First, before describing a detailed configuration of the connector apparatus according to the first embodiment of the present invention, an overview of an overall configuration of the endoscope apparatus provided with the connector apparatus will be described using mainly FIG. 1. FIG. 1 is an external perspective view illustrating a schematic configuration of the endoscope apparatus provided with the connector apparatus according to the first embodiment of the present invention.

The endoscope apparatus 1 mainly includes an endoscope 2, an image processing apparatus 3, which is an external device, and a display apparatus 4 or the like.

The connector apparatus of the present embodiment includes a plug 20 provided at an end part of a wiring cable (universal cord 16) extending from the endoscope 2 in the above endoscope apparatus 1 and a receptacle 31 disposed on a casing front face 30 of an external device (image processing apparatus 3).

In the endoscope apparatus 1, the endoscope 2 is a component including an image pickup unit configured to pick up an image of a desired observation region in a subject of a living body or an object of a structure. The endoscope 2 mainly includes an insertion portion 12, an operation portion 13, the universal cord 16 and the plug 20.

Of these components, the plug 20 is a constituting unit that constitutes part of the connector apparatus of the present embodiment. The plug 20 is provided at an end part of the universal cord 16, which is a wiring cable extending from the endoscope 2. The plug 20 includes a substantially cylindrical plug shaft 20a and a plug body part 20b having a substantially cylindrical shape as a whole. The plug 20 is connected to the receptacle 31 disposed on the casing front face 30 of the image processing apparatus 3 as an external device.

The universal cord 16 is a wiring cable configured to connect the operation portion 13 and the image processing apparatus 3. A signal line or the like such as an electric signal line and an optical fiber cable is inserted through the universal cord 16. The electric signal line and the signal line of the optical fiber cable or the like are inserted through the insertion portion 12 via the operation portion 13. In this case, for example, one end of the optical fiber cable is disposed in the plug 20 and the other end of the optical fiber cable is disposed in a distal end portion 21 of the insertion portion 12 of the endoscope 2.

Note that the insertion portion 12 includes the distal end portion 21 and a flexible tube portion 22 including a bending portion and a proximal end of the insertion portion 12 is connected to the operation portion 13. The operation portion 13 is a region provided with an operation member on an outer surface and grasped by a user. The insertion portion 12 is connected at one end of the operation portion 13 and the universal cord 16 is connected at the other end.

With such a configuration, the signal line or the like such as the electric signal line and the optical fiber cable, which is inserted from the insertion portion 12 through the universal cord 16 via the operation portion 13 in the endoscope 2, is electrically connected to the image processing apparatus 3 via the connector apparatus of the present embodiment. Such a configuration makes it possible to transmit image pickup data acquired by the endoscope 2 from the endoscope 2 to the image processing apparatus 3 and transmit various kinds of control signals of the endoscope 2 from the image processing apparatus 3.

The image processing apparatus 3 is a control unit configured to process various kinds of signals such as image pickup data acquired by the endoscope 2 or perform control processing of the endoscope 2. The receptacle 31 is disposed at an opening with which the above plug 20 engages on the casing front face 30 of the image processing apparatus 3.

The receptacle 31 is a constituting unit that constitutes another part of the connector apparatus of the present embodiment. The receptacle 31 includes a plug shaft insertion receiving portion 34, a plug body receiving portion 35 and the like. The receptacle 31 is configured so that the above plug 20 provided at the end part of the universal cord 16 of the endoscope 2 is connected.

In other words, the above connector apparatus of the present embodiment is a constituting unit including the above plug 20 and the above receptacle 31. In the connector apparatus, the above plug 20 is fitted into and connected to the above receptacle 31 to thereby connect the endoscope 2 and the image processing apparatus 3.

An operation display panel unit 32 formed of various operation members and state display members (LED or the like) and a power switch 33 or the like are provided on the casing front force 30 of the image processing apparatus 3.

The above endoscope apparatus 1 is schematically configured as described above. Note that the rest of the configuration of the endoscope apparatus 1 is assumed to be substantially the same as configurations of conventional and popular endoscope apparatuses, and so detailed description is omitted.

Figure 2:
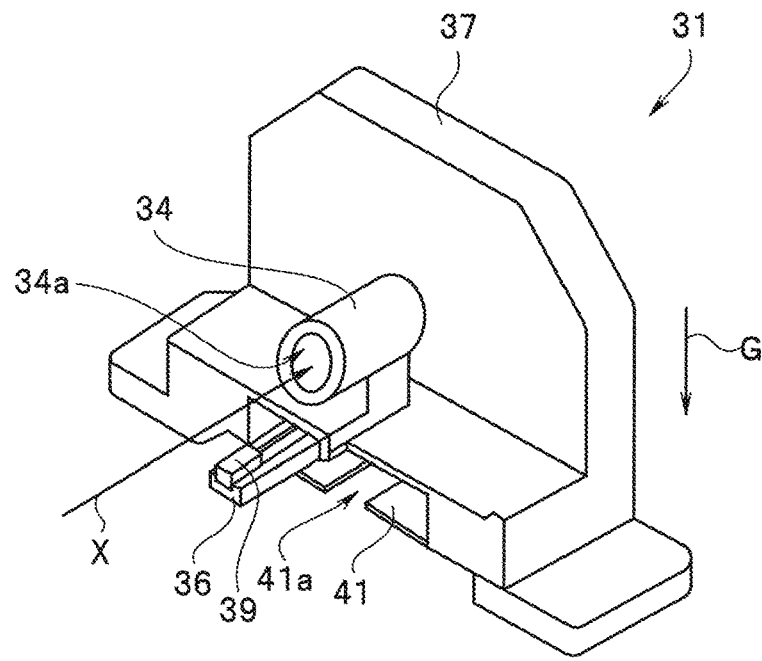
FIG. 2 is an external perspective view illustrating a schematic configuration of a receptacle of the connector apparatus of the first embodiment of the present invention.

Next, a specific configuration of the connector apparatus according to an embodiment of the present invention will be described. FIG. 2 is an external perspective view illustrating a schematic configuration of a receptacle of the connector apparatus of the present embodiment. Note that in FIG. 2, illustrations of some components (e.g., the plug body receiving portion 35) are omitted.

Figure 3:
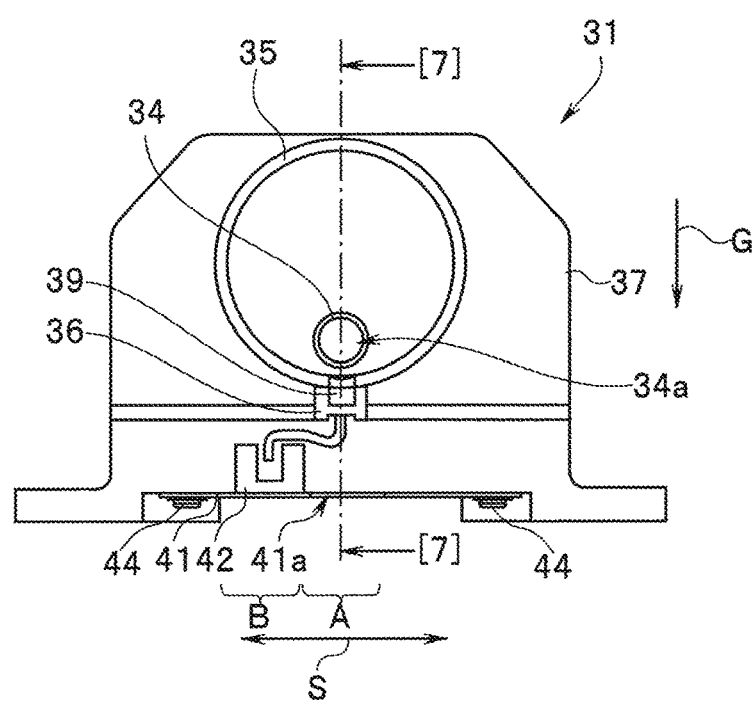
FIG. 3 is a schematic front view illustrating a front of the receptacle in FIG. 2.
Figure 4:
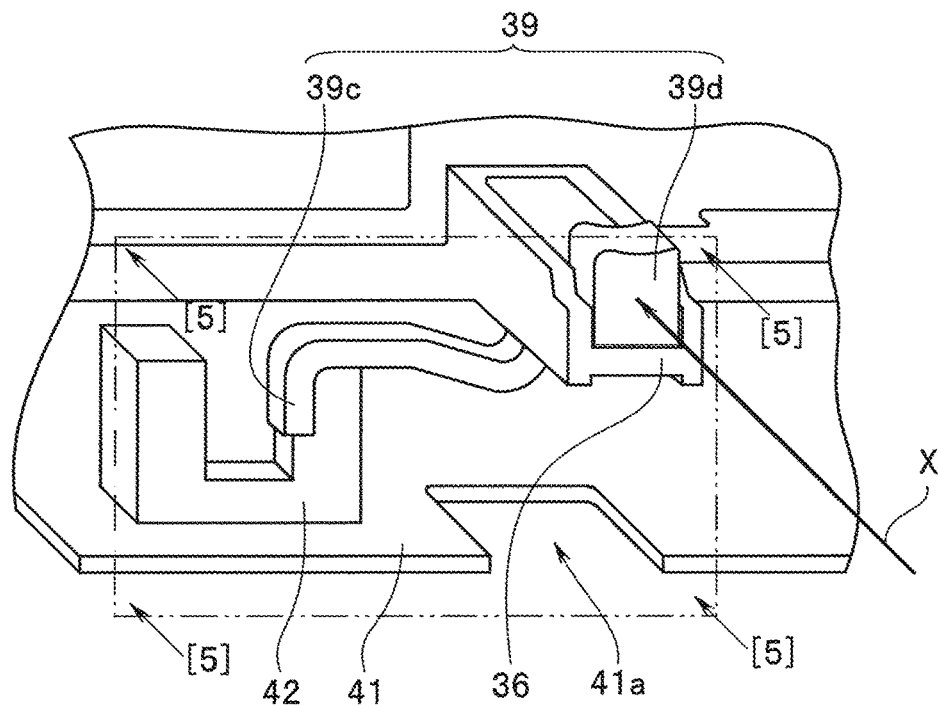
FIG. 4 is an enlarged perspective view of main parts of a plug detection sensor unit in the receptacle in FIG. 2.
Figure 5:
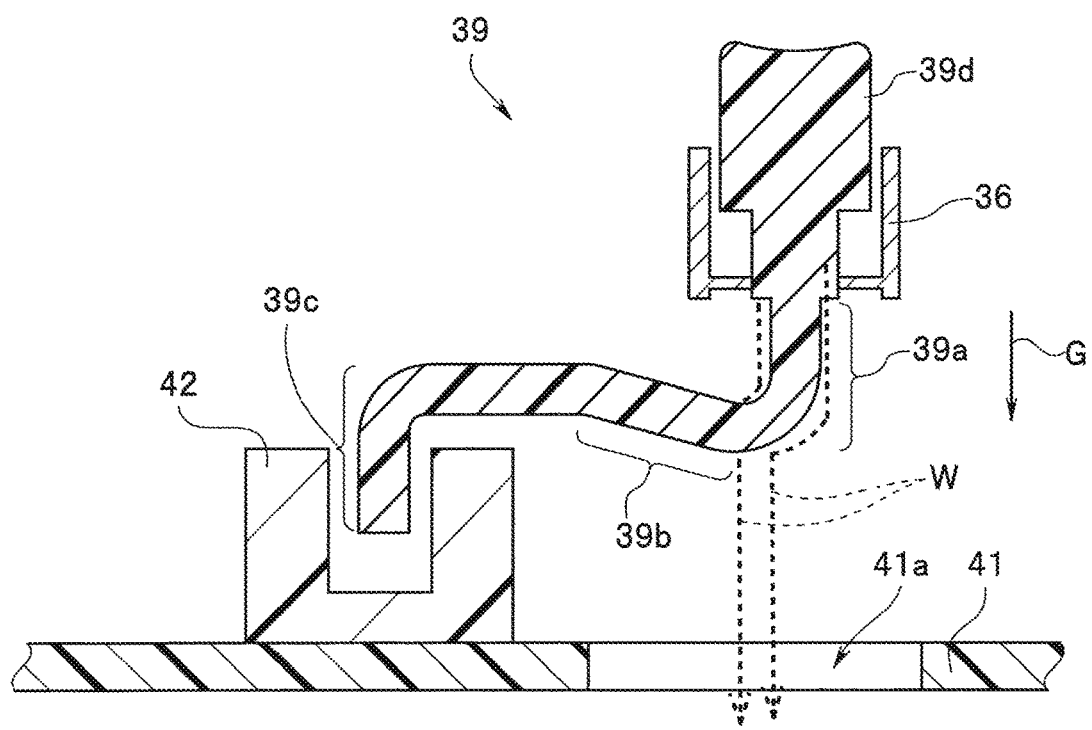
FIG. 5 is a cross-sectional view cut along a cross section indicated by arrowed reference numeral "5" in FIG. 4 and shown by a two-dot dashed line.
Figure 6:
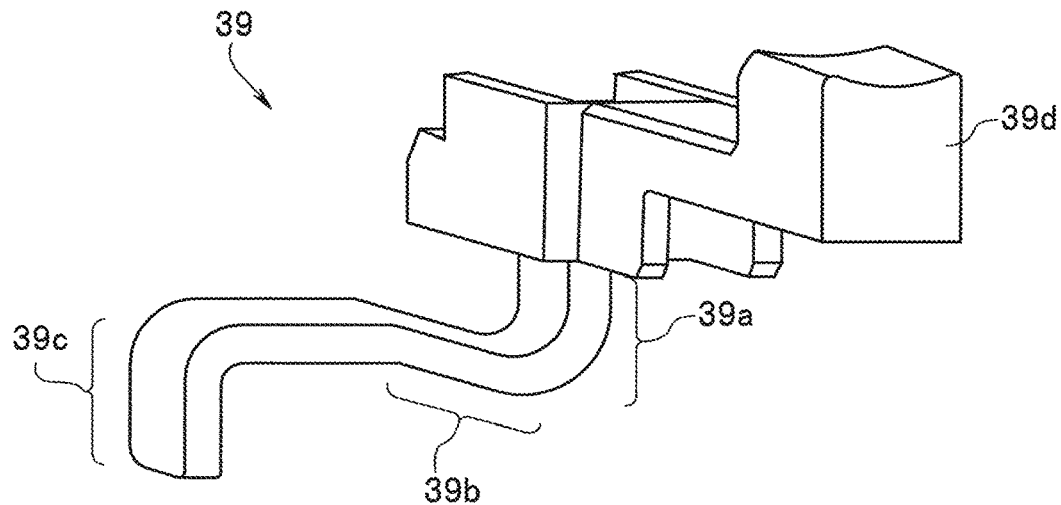
FIG. 6 is an enlarged perspective view of main parts of only the moving member of the plug detection sensor unit extracted from the receptacle in FIG. 2.

FIG. 3 is a schematic front view illustrating a front face of the receptacle in FIG. 2. FIG. 4 is an enlarged perspective view of main parts of a plug detection sensor unit in the receptacle in FIG. 2. FIG. 5 is a cross-sectional view of the plug detection sensor unit cut along a cross section shown by a two-dot dashed line and indicated by an arrowed reference numeral "5" in FIG. 4. FIG. 6 is an enlarged perspective view of main parts of only the moving member of the plug detection sensor unit extracted from the receptacle in FIG. 2.

As shown in FIG. 2 and FIG. 3, the receptacle 31 of the connector apparatus of the present embodiment mainly includes a receptacle body 37, an electric substrate 41 and plug detection sensor units (39, 42).

The receptacle body 37 includes a socket portion configured to engage with and receive the plug 20. The socket portion of the receptacle body 37 is formed of the plug shaft insertion receiving portion 34, the plug body receiving portion 35 and a moving member guide portion 36.

The plug shaft insertion receiving portion 34 is a region into which the plug shaft 20a of the plug 20 is fitted. An insertion hole 34a through which the plug shaft 20a is inserted is formed in the plug shaft insertion receiving portion 34. The insertion hole 34a is a through hole extending in a direction along an insertion direction (arrow X direction in FIG. 2) of the plug 20.

The plug body receiving portion 35 is a region into which the plug body part 20b of the plug 20 is fitted. The plug body receiving portion 35 is formed so as to cover part of an outer circumferential surface of the plug body part 20b when the plug 20 is inserted through the receptacle 31.

The moving member guide portion 36 of the receptacle body 37 is a guide portion configured to slidably hold part (holding portion 39d; which will be described later) of a moving member 39 (one of components of the plug detection sensor unit), which will be described later and guide the moving member 39 only in a direction along the insertion direction (arrow X direction in FIG. 2) of the above plug 20. The moving member guide portion 36 is formed in the vicinity of the above plug shaft insertion receiving portion 34 and at a lower part in a vertical direction (see arrowed reference character G in FIG. 2 and FIG. 3) of the plug shaft insertion receiving portion 34.

The electric substrate 41 is a plate-shaped part configured to fix and mount a plurality of electric parts including a sensor element 42, which will be described later. The electric substrate 41 is fixed to the receptacle body 37 using screws 44 or the like (see FIG. 3). In that case, the electric substrate 41 is fixedly disposed at a lower part in the vertical direction G with respect to the plug shaft insertion receiving portion 34 and the moving member guide portion 36. The sensor element 42 (one of the components of the plug detection sensor unit), which will be described later, is disposed at a predetermined position of the electric substrate 41 (details will be described later).

The electric substrate 41 is formed so as to include a notch 41a, which is a partially cut-out portion (see FIG. 4). Here, when the electric substrate 41 is fixed to the receptacle body 37 by the screws, the notch 41a of the electric substrate 41 is disposed at a lower part region A (see FIG. 3) in the vertical direction G with respect to the plug shaft insertion receiving portion 34 and the moving member guide portion 36. In other words, the notch 41a is disposed at a lower part in the vicinity of a connection portion between a first portion 39a and a second portion 39b (details will be described later) of the moving member 39 in the vertical direction G, which will be described later.

Note that the electric substrate 41 may be formed of a rigid substrate or a flexible substrate.

The plug detection sensor unit is a mechanical unit configured to detect that the plug 20 has been fitted into the receptacle 31. The plug detection sensor unit includes the moving member 39 and the sensor element 42.

The moving member 39 is a member configured to move, when the plug 20 is inserted into the receptacle 31 in a predetermined insertion direction (direction along the arrow X) and part of the plug body part 20b comes into contact with the receptacle 31, in the same direction (X direction) in conjunction with movement of the plug 20. The moving member 39 has a function of acting on the sensor element 42 and detecting that the plug 20 has been fitted into the receptacle 31 (the plug 20 is located in the receptacle 31) during the movement.

Thus, the moving member 39 is formed in a shape as shown in FIG. 4 to FIG. 6. In other words, the moving member 39 of the receptacle 31 of the connector apparatus of the present embodiment is formed by including the first portion 39a, the second portion 39b, a third portion 39c and a holding portion 39d.

Here, the holding portion 39d of the moving member 39 is a region held by the moving member guide portion 36 of the receptacle body 37 slidably in the predetermined direction (X direction). The holding portion 39d is disposed at a predetermined position in the receptacle 31 such that part of the plug body part 20b comes into contact when the plug 20 is inserted into the receptacle 31. With such a configuration, when the plug 20 is inserted into the receptacle 31 and the plug 20 moves in the predetermined direction (X direction), the moving member 39 is configured to move in the same direction in conjunction with movement of the plug 20.

The first portion 39a of the moving member 39 is a region, which comes into contact with the above moving member guide portion 36, that is, a region which extends downward in the vertical direction G from the vicinity of the above holding portion 39d.

The second portion 39b of the moving member 39 is a region, which includes one end and the other end, and is formed such that the one end is connected to the first portion 39a and the other end is located above the one end. Note that although a case has been described in the present embodiment where one end of the second portion 39b is connected to a bottom end of the first portion 39a, one end of the second portion 39b only needs to be connected to the first portion 39a without being limited to this mode.

The third portion 39c of the moving member 39 is a region formed by including one end and the other end, with the one end connected to the second portion 39b and the other end extending downward in the vertical direction G. Note that although a case has been described in the present embodiment as an example where one end of the third portion 39c is connected to one end of the second portion 39b, the one end of the third portion 39c only needs to be connected to the second portion 39b without being limited to this mode.

When the moving member 39 moves in the predetermined direction (X direction) in conjunction with insertion of the plug 20 into the receptacle 31, the third portion 39c is a region configured to move between a state of acting on the sensor element 42 and a state of not acting on the sensor element 42.

In this case, when the third portion 39c turns from the state of not acting on the sensor element 42, through the state of acting on the sensor element 42 to the state of not acting on the sensor element 42 again, the plug 20 is assumed to be in a first state (which will be described later; an engagement state shown in FIG. 9) disposed in a predetermined region in the receptacle 31.

When the third portion 39c is in the state of not acting on the sensor element 42 (the state in FIG. 7), the plug 20 is assumed to be in a second state in which it is not disposed in the predetermined region in the receptacle 31 (non-engagement state shown in FIG. 7, which will be described later).

Therefore, by moving in the predetermined direction (X direction) in conjunction with the insertion of the plug 20 into the receptacle 31, the above third portion 39c constitutes a region of causing the sensor element 42 to detect the first state and the second state of the plug 20.

The sensor element 42 is an electric part mounted on the electric substrate 41 and configured to detect presence or absence of an object (more specifically the plug 20) in a predetermined region in the receptacle 31. In the connector apparatus of the present embodiment, the sensor element 42 is located below the plug shaft insertion receiving portion 34 and the moving member guide portion 36 of the receptacle 31 and disposed at a position (see a region shown by reference character B in FIG. 3) apart by a predetermined distance from the region below (see reference character A shown in FIG. 3) the plug shaft insertion receiving portion 34 and the moving member guide portion 36 in the vertical direction G in a direction orthogonal to the vertical direction G (see reference character S shown in FIG. 3). In other words, the sensor element 42 is disposed in a region other than the region directly below the plug shaft insertion receiving portion 34 or the like. Note that a U-shaped (having a concave cross section) photoelectric sensor (beam sensor) or the like is applied to the sensor element 42.

When the third portion 39c of the moving member 39 acts at predetermined timing, the sensor element 42 detects that the plug 20 has been fitted into the receptacle 31 (that the plug 20 is present in the receptacle 31).

In other words, when the plug 20 is inserted into the receptacle 31, if the moving member 39 moves in the same direction in conjunction with the movement of the plug 20 in the predetermined direction (X direction), the third portion 39c of the moving member 39 also moves in the same direction. At this time, the third portion 39c of the moving member 39 moves from the position at which it does not act on the sensor element 42 (second state in FIG. 7 and FIG. 8), passes through the U-shaped (concave) portion of the sensor element 42 to act on the sensor element 42, and then moves again to a predetermined position at which it does not act on the sensor element 42 (first state in FIG. 9). Thus, the sensor element 42 detects the first state (FIG. 9) and the second state (FIG. 7) of the plug 20 in the receptacle 31.

Note that the sensor element 42 may be configured to have not only a function of performing insertion detection of the plug 20 by the action of the third portion 39*c* but also a function of determining a type of the plug inserted into the receptacle in addition to this.

More specifically, when the plug 20 is inserted into the receptacle 31 and both are in a final engagement state, if the state in which the third portion 39*c* is in the detection region of the sensor element 42 is maintained, the plug 20 currently inserted in the receptacle 31 is detected to be a "type A" plug. Similarly, when the plug 20 is inserted into the receptacle 31 and both are in a final engagement state, after the third portion 39*c* passes through the detection region of the sensor element 42, if the third portion 39*c* is outside the detection region, the plug 20 currently inserted in the receptacle 31 is detected to be a "type B" plug. The third portion 39*c* and the sensor element 42 may be provided with such a plug type determination function.

Figure 8:
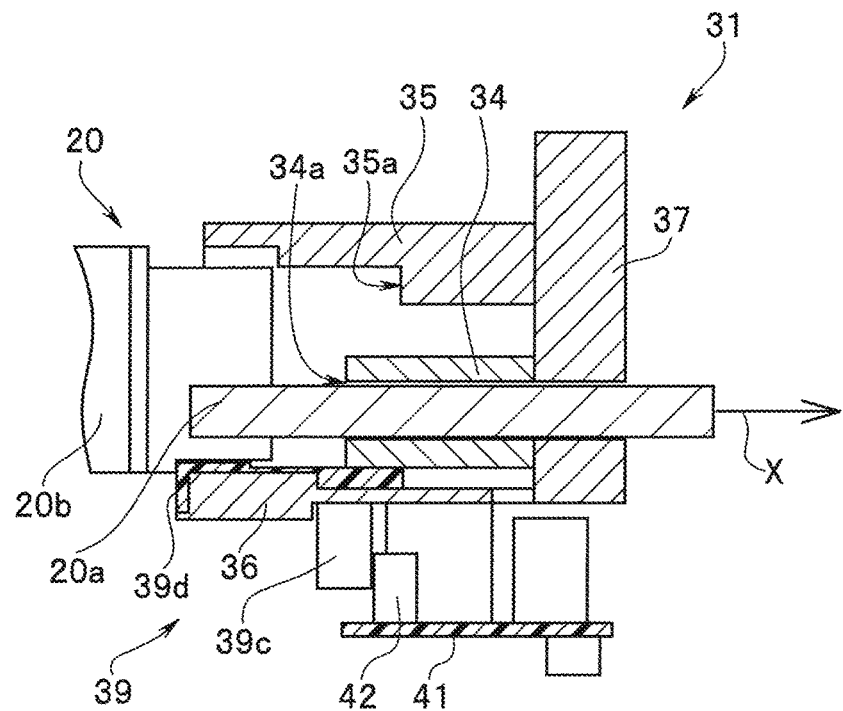
FIG. 8 is a diagram illustrating a state following the state in FIG. 7, and a state during insertion of the plug into the receptacle (state in which the plug is in contact with the moving member)
Figure 9:
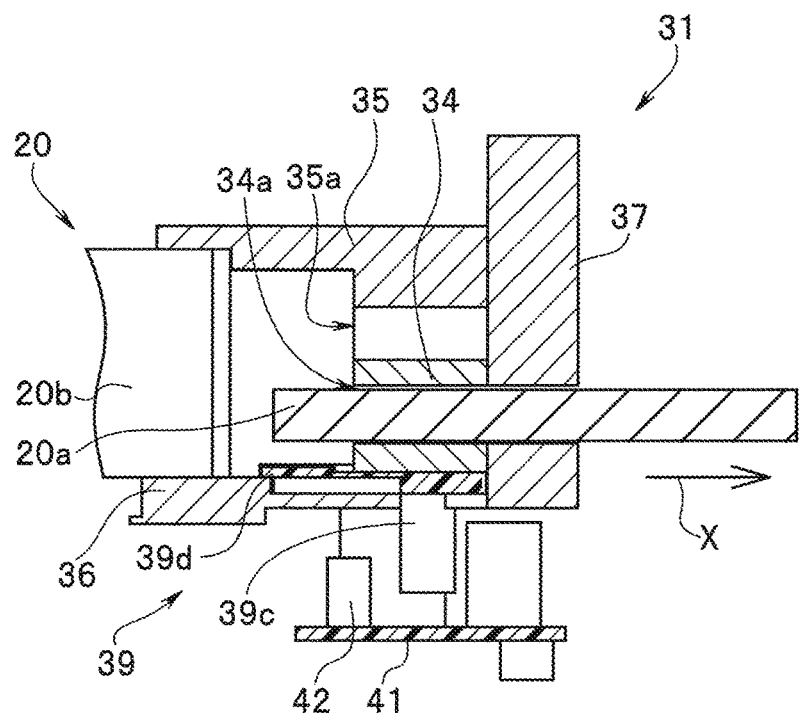
FIG. 9 is a diagram illustrating a state following the state in FIG. 8, and a state in which the insertion of the plug into the receptacle has been completed.

Operation of the connector apparatus of the present embodiment configured as described above will be described below. FIG. 7 to FIG. 9 are diagrams illustrating operation of inserting the plug into the receptacle of the connector apparatus of the present embodiment. Among those drawings, FIG. 7 is a diagram illustrating a state in an initial stage in which the plug is being inserted into the receptacle. FIG. 8 is a diagram illustrating a state during insertion of the plug into the receptacle (state in which the plug is in contact with the moving member). FIG. 9 is a diagram illustrating a state in which the insertion of the plug into the receptacle has been completed. Note that FIG. 7 to FIG. 9 each illustrate a cross-sectional view corresponding to a cross section along a line [7]-[7] in FIG. 3.

Figure 7:
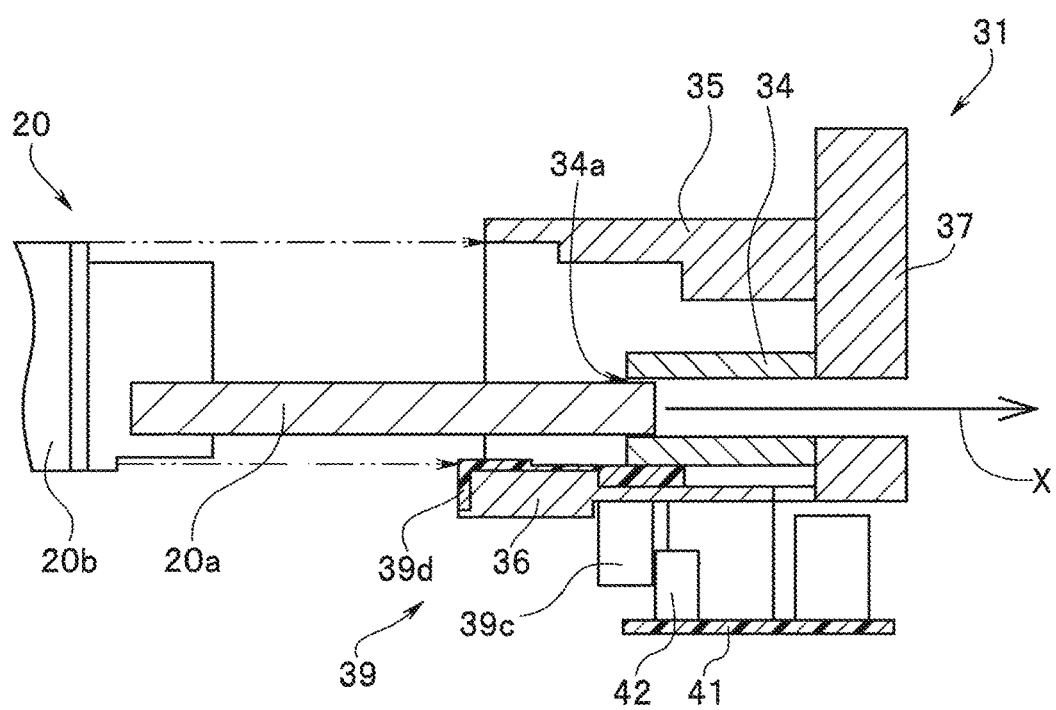
FIG. 7 is a diagram illustrating an operation of inserting the plug into the receptacle in the connector apparatus according to the first embodiment of the present invention, and illustrating a state in an initial stage in which the plug is being inserted into the receptacle.

First, in the connector apparatus of the present embodiment, when the plug 20 is inserted into the receptacle 31, the plug 20 is caused to move in the arrow X direction in FIG. 7 from the position at which the plug body part 20*b* is fitted into the plug body receiving portion 35 such that the plug shaft 20*a* is inserted into the insertion hole 34*a* of the plug shaft insertion receiving portion 34 as shown in FIG. 7.

When the plug shaft 20*a* is inserted into the insertion hole 34*a* of the plug shaft insertion receiving portion 34, the plug shaft 20*a* is guided by the insertion hole 34*a* by only pushing the plug 20 and inserted in the arrow X direction subsequently.

Eventually, as shown in FIG. 8, a portion a little closer to the bottom of a periphery portion on the front face of the plug body part 20*b* comes into contact with the front face of the holding portion 39*d* of the moving member 39. When the plug 20 is further pushed in the arrow X direction from this state, the moving member 39 moves in the arrow X direction along the moving member guide portion 36 in conjunction with the movement in the arrow X direction of the plug 20.

As shown in FIG. 9, part of the periphery portion on the front face of the plug body part 20*b* comes into contact with part of the plug body receiving portion 35 on the inner surface side (contacting portion shown by reference numeral 35*a* in FIG. 8 and FIG. 9), and the plug 20 is fixed at a predetermined position in the receptacle 31 by operation of a lock mechanism (not shown).

In this case, when moving from the state shown in FIG. 8 to the state shown in FIG. 9, the moving member 39 moves in the arrow X direction in conjunction with the movement of the plug 20 in the same direction. Along with this, the third portion 39*c* of the moving member 39 passes through the U-shaped (concave) portion of the sensor element 42.

In other words, in the states in FIG. 7 and FIG. 8, the third portion 39*c* of the moving member 39 is not acting on the U-shaped (concave) portion of the sensor element 42, and at this time, the plug 20 is in the second state in which it is not disposed in the predetermined region in the receptacle 31.

Note that the positional relationship between the third portion 39*c* and the sensor element 42 when the plug 20 is inserted into the receptacle 31 and the sensor element 42 detects that both are completely in an engagement state is not limited to the aforementioned example (where the third portion 39*c* passes through the sensor element 42).

The configuration may be such that, for example, when the plug 20 and the receptacle 31 are completely in an engagement state, the third portion 39*c* has advanced into the U-shaped (concave) portion of the sensor element 42 and is in a state in which the third portion 39*c* remains in the detection region of the sensor element 42 without passing through the U-shaped portion.

In this case, the configuration may be such that when the sensor element 42 detects that the third portion 39*c* continues to be disposed in the detection region of the U-shaped (concave) portion of the sensor element 42, that is, the sensor element 42 detects that the third portion 39*c* is continuously acting on the U-shaped (concave) portion of the sensor element 42, the sensor element 42 detects that the plug 20 and the receptacle 31 are completely in an engagement state (first state; in the state in FIG. 9).

On the other hand, the third portion 39*c* of the moving member 39 acts on the U-shaped (concave) portion of the sensor element 42 for a predetermined period after the state in FIG. 8. At this time, the plug 20 is in the first state in which the plug 20 is disposed in the predetermined region of the receptacle 31.

Thus, (the third portion 39*c* of) the moving member 39 detects the two states of the above plug 20 in the receptacle 31.

When the plug 20 is inserted into the receptacle 31, it is assumed that a liquid in a form such as a water droplet is attached to a circumferential surface of the plug shaft 20*a* of the plug 20.

Here, when the plug 20 is inserted into the receptacle 31, a water droplet (liquid) may infiltrate into the receptacle 31 via the plug shaft 20*a* to the plug shaft insertion receiving portion 34, the moving member guide portion 36 disposed below and an internal component such as the moving member 39 held to the moving member guide portion 36, and the water droplet may drop onto the electric substrate 41 provided inside the receptacle 31.

Thus, the connector apparatus of the present embodiment is configured by devising the shape of the moving member 39 so as to prevent a liquid such as a water droplet which has entered the receptacle 31 from the plug 20 via each component from dropping onto the electric substrate 41 and causing adverse influences.

In other words, the moving member 39 of the connector apparatus of the present embodiment is formed by providing the first portion 39*a,* the second portion 39*b* and the third portion 39*c.*

When the liquid attached to the plug shaft 20*a* of the plug 20 reaches the moving member 39, for example, via the plug shaft insertion receiving portion 34 and the moving member guide portion 36, the liquid flows downward from the holding portion 39d of the moving member 39 along the first portion 39a as shown by a broken line arrow W in FIG. 5 and falls down from the vicinity of the connection portion between the first portion 39a and the second portion 39b. At this time, as described above, and as shown in FIG. 5, the second portion 39b is formed such that one end of the second portion 39b is connected to (the bottom end of) the first portion 39a and the other end is located above the one end. Therefore, due to this shape, the liquid flowing down along the first portion 39a only falls down from the one end (connection portion with the first portion 39a) of the second portion 39b and never flows to the other end of the second portion 39b. Therefore, the above liquid never flows to the sensor element 42 via the moving member 39, and therefore the liquid infiltrating from the outside never adversely affects the sensor element 42.

Furthermore, the connector apparatus of the present embodiment is provided with the notch 41a of the electric substrate 41 in the region below the connection portion between the first portion 39a and the second portion 39b of the moving member 39 in the vertical direction G. Therefore, the liquid dropping down from the connection portion between the first portion 39a and the second portion 39b of the moving member 39, passes through the notch 41a and drops down below the electric substrate 41 without being attached to the electric substrate 41. This prevents the liquid from adversely affecting other electric parts on the electric substrate 41.

Note that the region below the notch 41a of the electric substrate 41 constitutes a bottom surface panel of the casing of the image processing apparatus 3 in which, for example, the connector apparatus is provided, and even if the liquid falls here, the connector apparatus is configured not to be affected at all. Therefore, it is preferable to avoid any other components from being disposed in the region below the notch 41a of the electric substrate 41. Any component can be disposed in the region below the notch 41a of the electric substrate 41 as long as such a component is not affected by attachment of a liquid or the like.

Furthermore, in this case, a liquid storing portion having a shape that allows the dropping liquid to be received and accumulated (e.g., a dish shape or box shape) may be provided in the region below the notch 41a of the electric substrate 41. In that case, a component capable of absorbing and storing a liquid or the like inside, such as a sponge may be disposed in the liquid storing portion.

Note that a configuration has been adopted in the aforementioned first embodiment where the electric substrate 41 is provided with the notch 41a and the notch 41a is disposed in the region below the connection portion between the first portion 39a and the second portion 39b of the moving member 39 in the vertical direction G, whereas the present invention may only be configured such that the electric substrate 41 is not disposed in the region below the connection portion between the first portion 39a and the second portion 39b of the moving member 39 in the vertical direction G, and the configuration is not limited to the configuration example of the aforementioned first embodiment.

For example, instead of forming the electric substrate 41 as one substrate, the electric substrate 41 may be formed of two different electric substrates and the two electric substrates may be disposed at a predetermined interval. In this case, a configuration may be such that a clearance space generated between the two electric substrates is disposed in the region below the connection portion between the first portion 39a and the second portion 39b of the moving member 39 in the vertical direction G. Such a configuration makes it possible to obtain exactly the same effects as the effects of the notch 41a in the above first embodiment.

Furthermore, for example, the electric substrate 41 on which the sensor element 42 is mounted and disposed may not be disposed in the region below the connection portion between the first portion 39a and the second portion 39b of the moving member 39 in the vertical direction G. In other words, such a configuration may also be adopted that no electric substrate 41 is disposed in the region below the connection portion between the first portion 39a and the second portion 39b of the moving member 39 in the vertical direction G.

As described above, according to the first embodiment, even in the case of a configuration of the connector apparatus including the plug 20 and the receptacle 31, in which the electric substrate 41 is provided below the receptacle 31 due to the parts layout in the receptacle 31, by devising the configuration of the plug detection sensor unit to detect the insertion state of the plug 20 in the receptacle 31 (shape of the moving member 39 and arrangement of the sensor element 42), it is possible to prevent transmission of the liquid entering the receptacle 31 from outside the receptacle 31 from the plug 20 via the components of the receptacle 31 and the moving member 39 or the like to the sensor element 42 of the plug detection sensor unit.

More specifically, the moving member 39 of the plug detection sensor unit is formed by including the first portion 39a extending downward from the vicinity of a contact region with the receptacle 31, the second portion 39b, one end of which is connected to (one end of) the first portion 39a and the other end of which is located above the one end, and the third portion 39c formed with one end connected to (one end of) the second portion 39b and the other end extending downward and configured to switch between a first state in which the plug 20 is disposed in the predetermined region and a second state in which the plug 20 is not disposed in the predetermined region by moving in conjunction with the insertion of the plug 20 into the receptacle 31.

The sensor element 42 of the plug detection sensor unit is disposed at a position apart from a path of the liquid infiltrating from outside. Such a configuration makes it possible to prevent the liquid infiltrating from outside from adversely affecting the sensor element 42.

Furthermore, while adopting the layout of disposing the electric substrate 41 mounted with the sensor element 42 or the like below the receptacle 31, the connector apparatus of the present embodiment is configured to form the notch 41a in the electric substrate 41 and dispose the notch 41a in the region below the connection portion between the first portion 39a and the second portion 39b of the moving member 39 in the vertical direction G.

When a liquid infiltrating into the receptacle 31 from outside falls down along the moving member 39, the connector apparatus of the present embodiment adopting such a configuration makes it possible to avoid the liquid from being attached to the electric substrate 41 by the notch 41a. Therefore, the liquid infiltrating from outside never causes adverse influences on the sensor element 42 and the electric substrate 41.

In addition, according to the configuration of the present embodiment, it is possible to extend the degree of freedom of the arrangement of the plug detection sensor unit and thereby secure the degree of freedom of the layout of various components in the periphery portion of the receptacle and prevent the scale of the receptacle per se from increasing.

[First Modification]

The shape of the moving member 39 of the plug detection sensor unit of the connector apparatus according to the present embodiment is not limited to the aforementioned illustration, but the moving member 39 may be formed in another shape.

Figure 10:
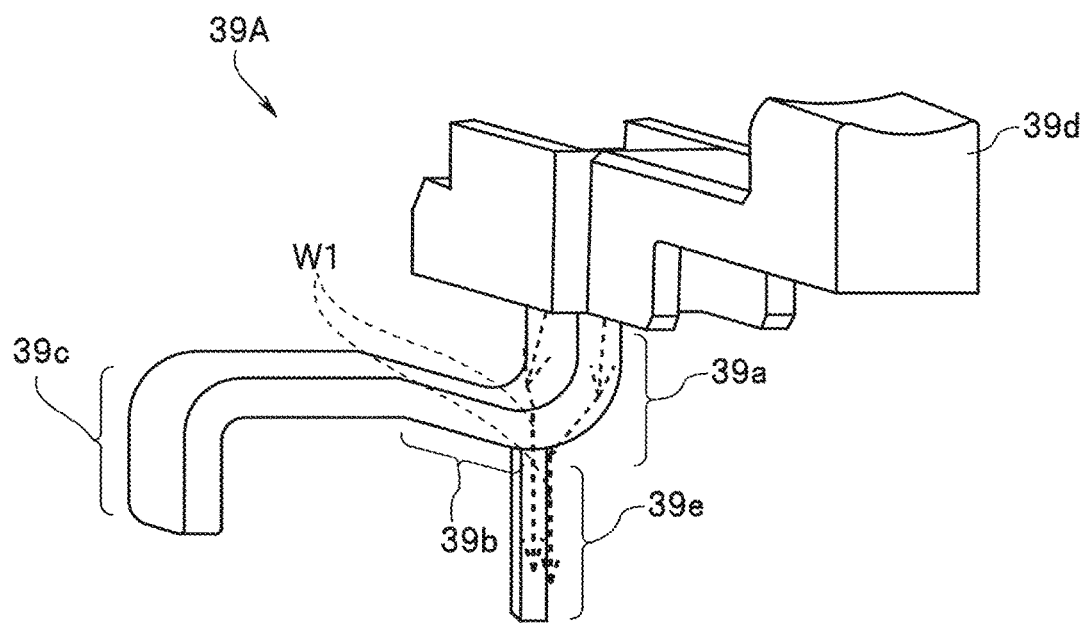
FIG. 10 is an external perspective view of main parts illustrating a first modification of the moving member of the connector apparatus according to the first embodiment of the present invention.

For example, FIG. 10 is an external perspective view of main parts illustrating a first modification of the moving member of the connector apparatus according to the first embodiment of the present invention.

Basically, the shape of a moving member 39A presented in the present modification is substantially the same as the shape applied in the aforementioned first embodiment as shown in FIG. 10.

In other words, the moving member 39A according to the present modification is formed by including the first portion 39a, the second portion 39b, the third portion 39c and the holding portion 39d.

In addition, the present modification is different in that a fourth portion 39e is further provided.

The above fourth portion 39e is a bar-shaped region formed so as to extend downward in the vertical direction G from the connection portion between the first portion 39a and the second portion 39b. By providing the fourth portion 39e, the liquid or the like flowing downward along the first portion 39a surely flows down along the fourth portion 39e as shown by a broken line arrow W1 in FIG. 10. The rest of the configuration is exactly the same as the configuration of the aforementioned first embodiment.

As described above, according to the above first modification, it is possible to obtain exactly the same effects as the effects of the above first embodiment.

By providing the fourth portion 39e in the moving member 39A in the above first modification, it is possible to cause the liquid or the like flowing down along the first portion 39a to further surely fall down using the fourth portion 39e.

[Second Modification]

Figure 11:
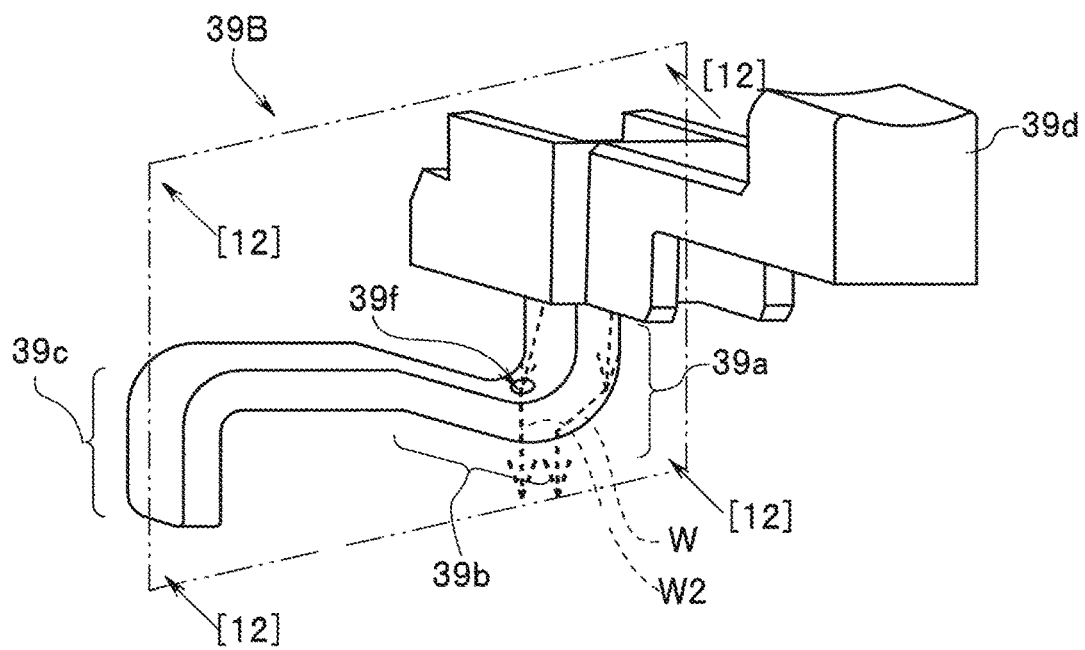
FIG. 11 is an external perspective view of main parts illustrating a second modification of the moving member of the connector apparatus according to the first embodiment of the present invention.
Figure 12:
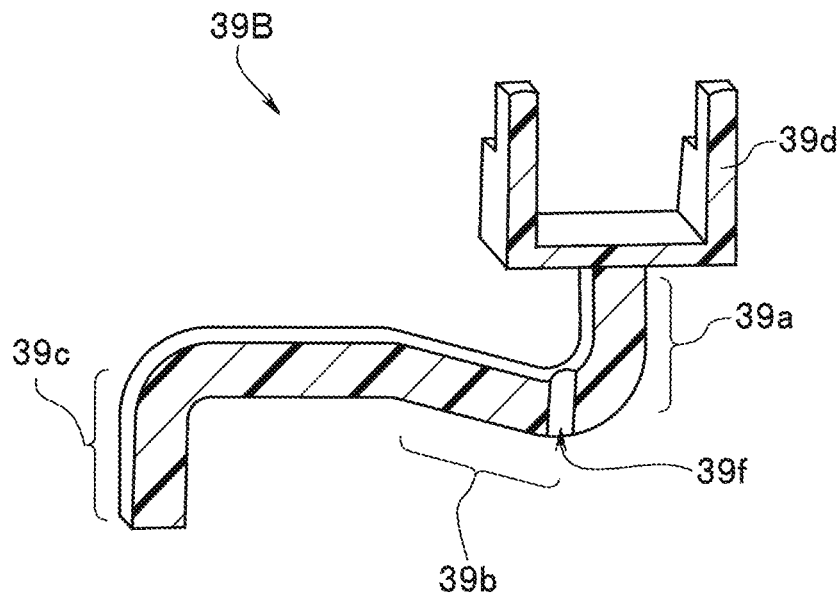
FIG. 12 is a three-dimensional cross-sectional view cut along a cross section indicated by an arrowed reference numeral "12" in FIG. 11 and shown by two-dot dashed line.

FIG. 11 is an external perspective view of main parts illustrating a second modification of the moving member of the connector apparatus according to the first embodiment of the present invention. FIG. 12 is a three-dimensional cross-sectional view of the moving member cut along a cross section indicated by an arrowed reference numeral "12" in FIG. 11 and shown by two-dot dashed line.

As shown in FIG. 11 and FIG. 12, basically, the shape of a moving member 39B presented in the present modification is substantially the same as the shape applied in the aforementioned first embodiment.

In other words, the moving member 39B according to the present modification is formed by including the first portion 39a, the second portion 39b, the third portion 39c and the holding portion 39d.

In addition, the present modification is different in that a through hole 39f penetrating downward in the vertical direction G is further provided in the vicinity of the connection portion between the first portion 39a and the second portion 39b.

By providing the above through hole 39f, part of the liquid or the like flowing down along the first portion 39a surely flows down through the through hole 39f as shown by a broken line arrow W2 in FIG. 11. The rest of the configuration is exactly the same as the configuration of the aforementioned first embodiment.

As described above, according to the above second modification, it is possible to obtain exactly the same effects as the effects of the aforementioned first embodiment.

Furthermore, in the above second modification, by providing the through hole 39f in the moving member 39B, it is possible to cause the liquid or the like flowing down along the first portion 39a to further surely flow down through the through hole 39f.

[Third Modification]

Figure 13:
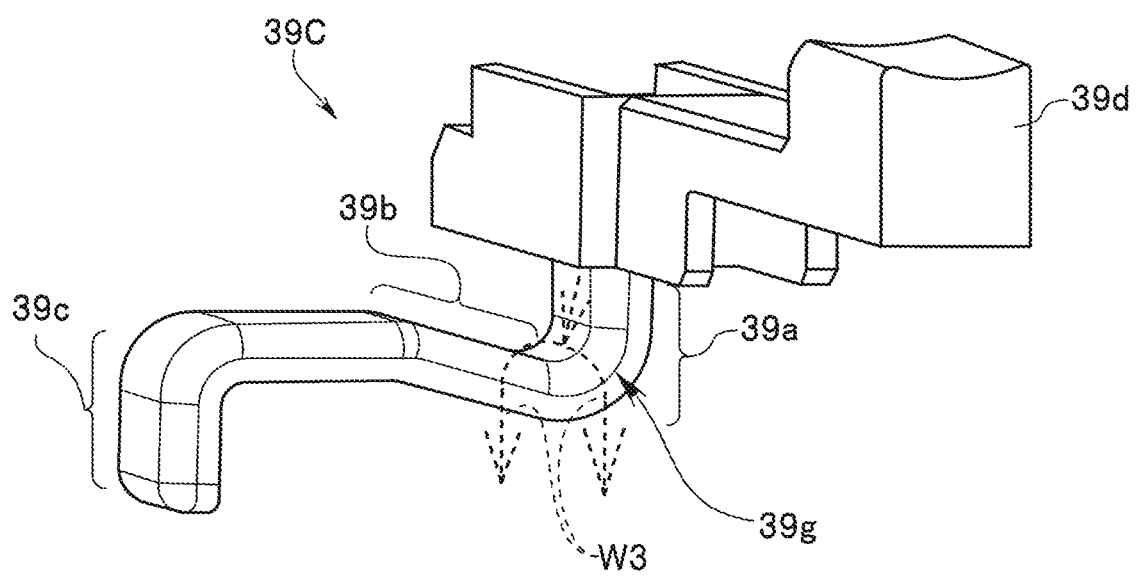
FIG. 13 is an external perspective view of main parts illustrating a third modification of the moving member of the connector apparatus according to the first embodiment of the present invention.

FIG. 13 is an external perspective view of main parts illustrating a third modification of the moving member of the connector apparatus according to the first embodiment of the present invention.

Basically, the shape of a moving member 39C presented in the present modification is substantially the same as the shape applied in the aforementioned first embodiment as shown in FIG. 13.

In other words, the moving member 39C according to the present modification is formed by including the first portion 39a, the second portion 39b, the third portion 39c and the holding portion 39d.

In addition, the present modification is different in that a cross-sectional shape of a side face 39g in the vicinity of at least the connection portion between the first portion 39a and the second portion 39b is formed into an R shape.

By adopting the above side face 39g having an R-shaped cross section, the liquid or the like flowing down along the first portion 39a smoothly and surely flows down along the side face 39g in the vicinity of the connection portion between the first portion 39a and the second portion 39b as shown by a broken line arrow W3 in FIG. 13. The rest of the configuration is exactly the same as the configuration of the aforementioned first embodiment.

As described above, according to the above third modification, it is possible to obtain exactly the same effects as the effects of the aforementioned first embodiment.

Furthermore, in the above third modification, by forming the side face 39g at least in the vicinity of the connection portion between the first portion 39a and the second portion 39b so as to have the R-shaped cross section in the moving member 39C, it is possible to cause the liquid or the like flowing down along the first portion 39a to flow down further smoothly and securely.

[Fourth Modification]

Figure 14:
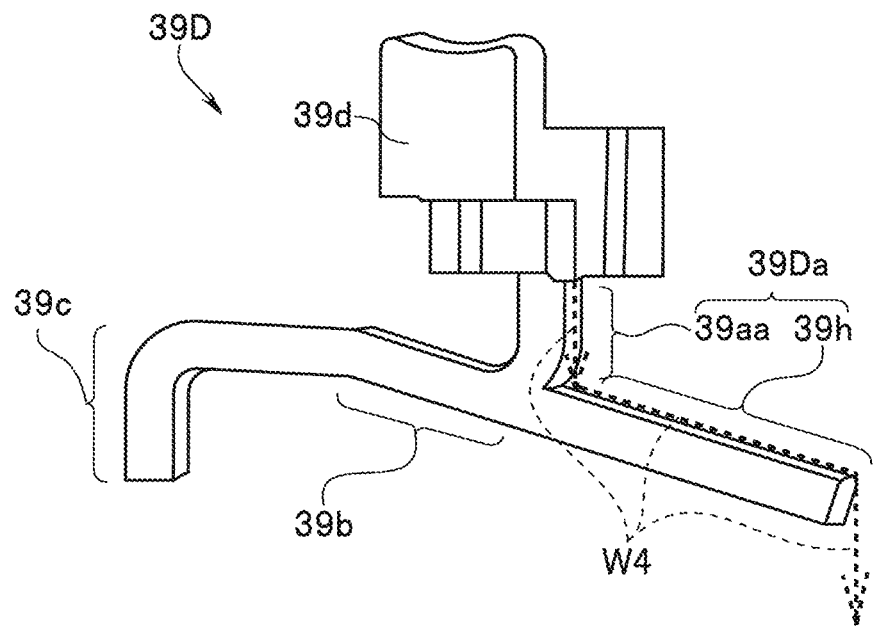
FIG. 14 is an external perspective view of main parts illustrating a fourth modification of the moving member of the connector apparatus according to the first embodiment of the present invention.

FIG. 14 is an external perspective view of main parts illustrating a fourth modification of the moving member of the connector apparatus according to the first embodiment of the present invention.

Basically, the shape of a moving member 39D presented in the present modification is substantially the same as the shape applied in the aforementioned first embodiment as shown in FIG. 14.

In other words, the moving member 39D according to the present modification is formed by including a first portion 39Da, the second portion 39b, the third portion 39c and the holding portion 39d.

The first portion 39Da according to the present modification is different in that it includes a first bar-shaped portion 39aa and a second bar-shaped portion 39h as shown in FIG. 14.

The first bar-shaped portion 39aa of the first portion 39Da extends from the holding portion 39d downward in the vertical direction and formed in a bar shape. The second portion 39b is connected to the first bar-shaped portion 39aa. An example of the second portion 39b is shown in the present modification where the second portion 39b is connected to a bottom end of the first bar-shaped portion 39aa. Note that the connection portion between the first portion 39Da and the second portion 39b is not limited to this illustration.

The second bar-shaped portion 39*h* of the first portion 39Da is a bar-shaped region extending from the connection portion between the first bar-shaped portion 39*a* and the second portion 39*b*. The second bar-shaped portion 39*h* is formed so as to extend, for example, diagonally downward such that one end of the second bar-shaped portion 39*h* is connected to a vicinity of the connection portion between the first bar-shaped portion 39*aa* of the first portion 39Da and the second portion 39*b* and the other end is located lower than the connection portion between the first bar-shaped portion 39*aa* and the second portion 39*b*.

By forming the first portion 39Da provided with the second bar-shaped portion 39*h* in such a form, a liquid or the like flowing down along the first bar-shaped portion 39*aa* gently and surely flows down along the second bar-shaped portion 39*h* as shown by a broken line arrow W4 in FIG. 14. In this case, the notch 41*a* of the electric substrate 41 is preferably disposed in a region from the region below the connection portion between the first portion 39Da and the second portion 39*b* in the vertical direction to a region reaching the region below the other end (lower portion) of the second bar-shaped portion 39*h* of the first portion 39Da in the vertical direction. The rest of the configuration is exactly the same as the aforementioned first embodiment.

As described above, according to the above fourth modification, it is possible to obtain exactly the same effects as the effects of the aforementioned first embodiment.

Furthermore, in the above fourth modification, by providing the second bar-shaped portion 39*h* in the first portion 39Da of the moving member 39D, it is possible to cause a liquid or the like flowing down along the first bar-shaped portion 39*aa* of the first portion 39Da to gently and surely to flow down using the second bar-shaped portion 39*h*.

[Fifth Modification]

Figure 15:
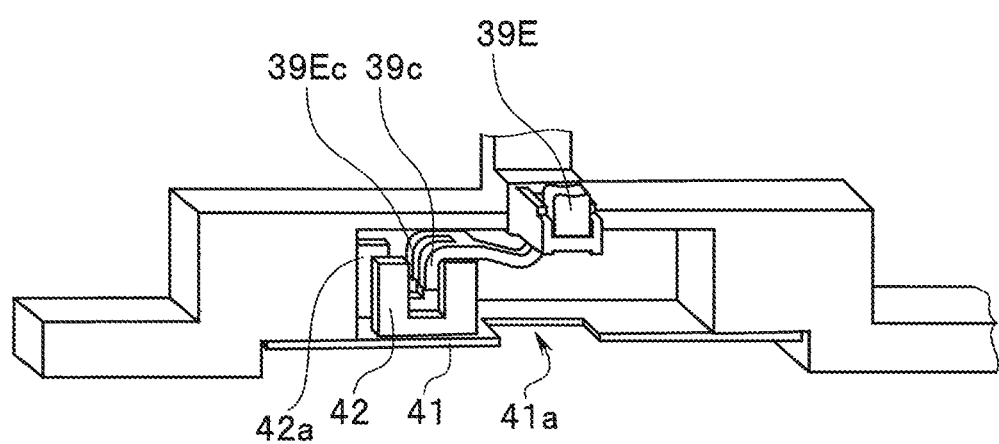
FIG. 15 is an external perspective view of main parts illustrating a fifth modification of the moving member of the connector apparatus according to the first embodiment of the present invention.

FIG. 15 is an external perspective view of main parts illustrating a fifth modification of the moving member of the connector apparatus according to the first embodiment of the present invention;

In the present modification, the moving member is constructed by including a plurality of plug detection sensor units. Thus, a moving member 39E is formed by including a plurality of (two in the present example) third portions 39*c* and 39Ec. In correspondence with this, a plurality of (two in the present example) sensor elements 42 and 42*a* are provided on the electric substrate 41. The rest of the configuration is exactly the same as the aforementioned first embodiment.

Here, basically, the shape of the moving member 39E is substantially the same as the shape applied in the aforementioned first embodiment as shown in FIG. 15, but the moving member 39E is different in that the plurality of (two) third portions 39*c* and 39Ec are integrally formed. One end of each of the plurality of (two) third portions 39*c* and 39Ec is connected to (one end of) the second portion 39*b* and the other end is formed so as to extend downward.

The plurality of (two) third portions 39*c* and 39Ec are disposed side by side parallel to the insertion direction of the plug 20 (arrow X direction). In correspondence with this, the plurality of (two) sensor elements 42 and 42*a* are also disposed side by side parallel to the same direction (insertion direction of the plug 20 (arrow X direction)).

Furthermore, in the present modification, the plurality of (two) third portions 39*c* and 39Ec and the plurality of (two) sensor elements 42 and 42*a* are arranged at equal intervals.

With such a configuration, at the same timing at which the one third portion 39*c* acts on the one sensor element 42, the other third portion 39Ec acts on the other sensor element 42*a*.

Therefore, for example, even when the one sensor element 42 malfunctions, the other sensor element 42*a* can detect the insertion of the plug 20.

As described above, according to the above fifth modification, it is possible to obtain exactly the same effects as the effects of the aforementioned first embodiment.

Furthermore, since the above fifth modification is configured such that a plurality of plug detection sensor units are provided so as to be able to perform detection at the same timing, even if the one plug detection sensor unit malfunctions, the other plug detection sensor unit can perform predetermined detection.

[Sixth Modification]

Figure 16:
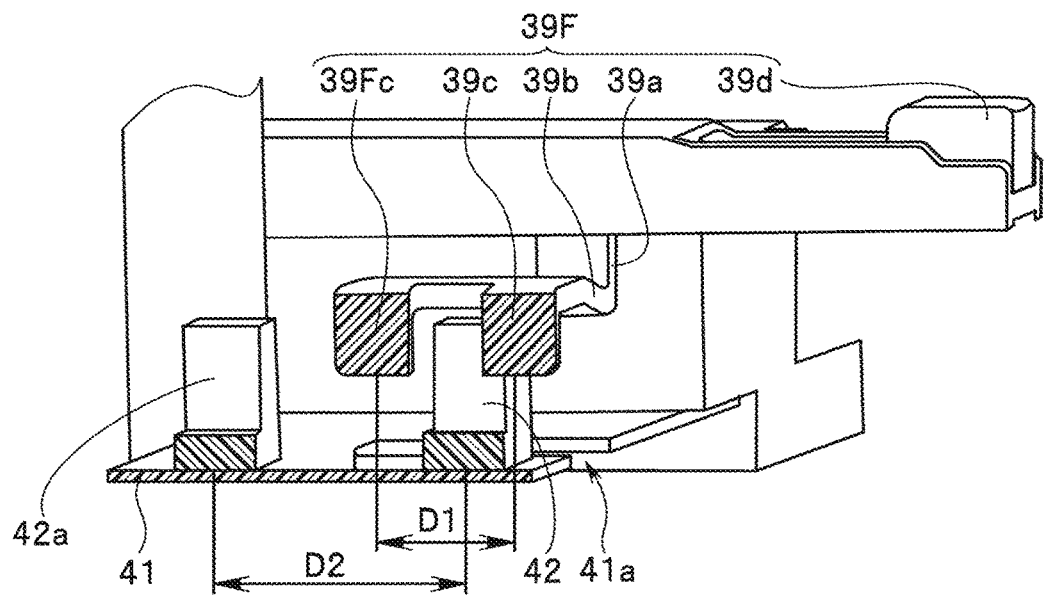
FIG. 16 is an external perspective view of main parts illustrating a sixth modification of the moving member of the connector apparatus according to the first embodiment of the present invention.

FIG. 16 is an external perspective view of main parts illustrating a sixth modification of the moving member of the connector apparatus according to the first embodiment of the present invention.

The present modification basically has a configuration substantially the same as the configuration of the aforementioned fifth modification. As shown in FIG. 16, the present modification is different in that an interval D1 between a plurality of (two in the present example) third portions 39*c* and 39Fc is made to differ from an interval D2 between the plurality of (two in the present example) sensor elements 42 and 42*a*. The rest of the configuration is exactly the same as the configuration of the above fifth modification.

Since such a configuration is adopted, the other third portion 39Fc acts on the other sensor element 42*a* at timing different from timing at which the one third portion 39*c* acts on the one sensor element 42.

Therefore, although description is given without illustrations, for example, when there are a plurality of types of the plugs 20 to be inserted, it is assumed that when a first plug is inserted into the receptacle 31, the one third portion 39*c* acts on the one sensor element 42, and the other third portion 39Fc then acts on the other sensor element 42*a*, and the insertion is thereby completed.

By contrast, when a second plug is inserted into the same receptacle 31, it is assumed that the one third portion 39*c* acts on the one sensor element 42 and insertion is then completed before the other third portion 39Fc acts on the other sensor element 42*a*.

The plug detection sensor unit according to the present modification has such a configuration that a combination of sensors for detection differs depending on the plug to be inserted, and it is thereby possible to detect the type of a plug to be inserted.

As described above, according to the above sixth modification, it is possible to obtain exactly the same effects as the effects of the aforementioned first embodiment, and further when a plurality of types of plugs are selectively connected in the above sixth modification, it is possible to detect the type of a plug to be inserted.

[Seventh Modification]

Figure 17:
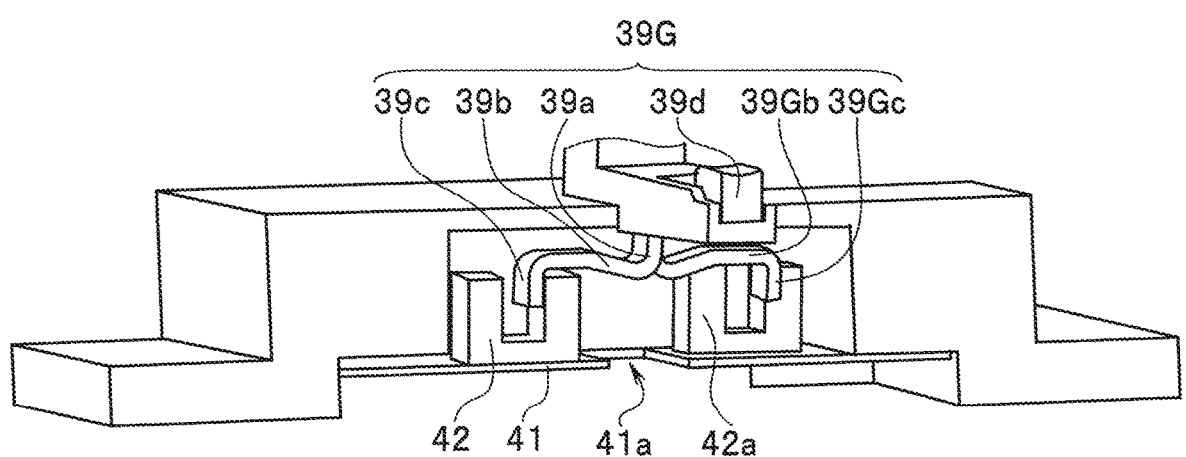
FIG. 17 is an external perspective view of main parts illustrating a seventh modification of the moving member of the connector apparatus according to the first embodiment of the present invention.

FIG. 17 is an external perspective view of main parts illustrating a seventh modification of the moving member of the connector apparatus according to the first embodiment of the present invention.

The present modification is similar to the above fifth and sixth modifications in that a plurality of plug detection sensor units are provided, whereas in the present modification, the plurality of (two in the present example) third portions 39*c* and 39Gc of the moving member 39G are different in arrangement from the plurality of (two in the present example) sensor elements 42 and 42*a* on the electric substrate 41. The rest of the configuration is exactly the same as the aforementioned first embodiment.

Here, basically, the shape of the moving member 39G is substantially the same as the shape applied in the aforementioned first embodiment as shown in FIG. 17, whereas the shape of the moving member 39G is different in that the plurality of (two) third portions 39*c* and 39G*c* are integrally formed. The plurality of (two) third portions 39*c* and 39G*c* are formed with one end connected to (one end of) the second portion 39*b* and the other end extending downward.

The plurality of (two) third portions 39*c* and 39G*c* are disposed side by side in a horizontal direction with respect to the insertion direction of the plug 20 (arrow X direction). In other words, the plurality of (two) third portions 39*c* and 39G*c* are formed so as to be substantially symmetric at positions facing each other across the first portion 39*a*. In correspondence with this, the plurality of (two) sensor elements 42 and 42*a* are also disposed side by side in the horizontal direction with respect to the same direction (insertion direction of the plug 20 (arrow X direction)).

Furthermore, the plurality of (two) third portions 39*c* and 39G*c* of the present modification are formed such that the third portions 39*c* and 39G*c* are located at the same position in the insertion direction of the plug 20. The plurality of (two) sensor elements 42 and 42*a* are also located at the same position in the insertion direction of the plug 20 accordingly.

With such a configuration, the other third portion 39G*c* acts on the other sensor element 42*a* at the same timing as the timing at which the one third portion 39*c* acts on the one sensor element 42.

Therefore, even when, for example, one sensor element 42 malfunctions, the other sensor element 42*a* can detect the insertion of the plug 20.

As described above, according to the above seventh modification, it is possible to obtain exactly the same effects as the effects of the aforementioned fifth modification.

Note that though not shown, the plurality of (two) third portions 39*c* and 39G*c* in the above seventh modification may be formed such that these third portions are located at different positions in the insertion direction of the plug 20. The positions of the plurality of (two) sensor elements 42 and 42*a* in the insertion direction of the plug 20 are also disposed accordingly.

Just as in the case of the above sixth modification, such a configuration makes it possible to detect the type of a plug inserted when a plurality of types of plugs are selectively connected.

Note that it goes without saying that in addition to the moving member of the above first embodiment, the above first to seventh modifications may be arbitrarily combined as appropriate and configured as a moving member.

[Second Embodiment]

Examples of the connector apparatus have been shown in the aforementioned first embodiment and modifications where the connector apparatus includes the plug 20 including the plug body part 20*b* in a cylindrical shape as a whole and the receptacle 31 including the plug body receiving portion 35 in a form corresponding to the shape of the plug 20 and in a cylindrical shape as a whole, but the configuration of the present invention is not limited to this.

A connector apparatus according to a second embodiment, which will be described next, is an example of a connector apparatus including a plug 20H including a plug body part 20H*b* having a substantially rectangular, cylindrical cross section as a whole and a receptacle 31H including a plug body receiving portion 35H having a rectangular, cylindrical cross section in a form corresponding to the shape of the plug 20H.

Figure 18:
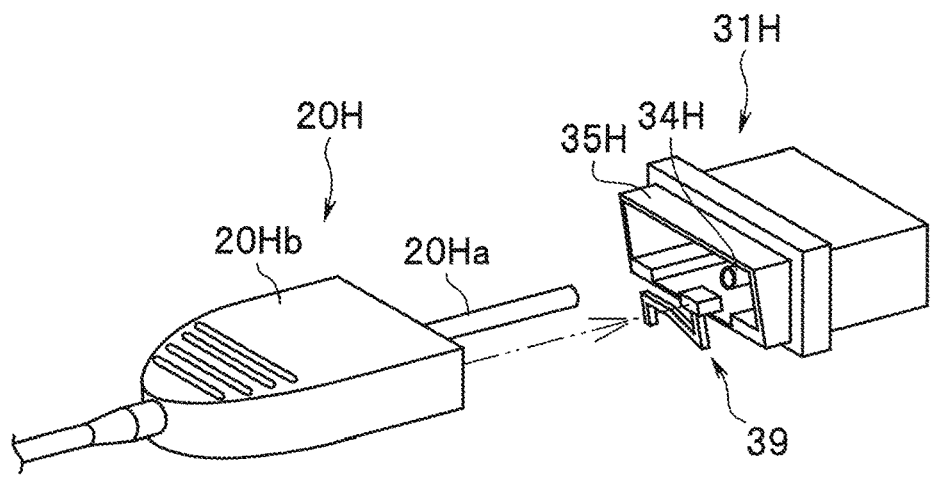
FIG. 18 is an external perspective view schematically illustrating a configuration of a connector apparatus according to a second embodiment of the present invention.
Figure 19:
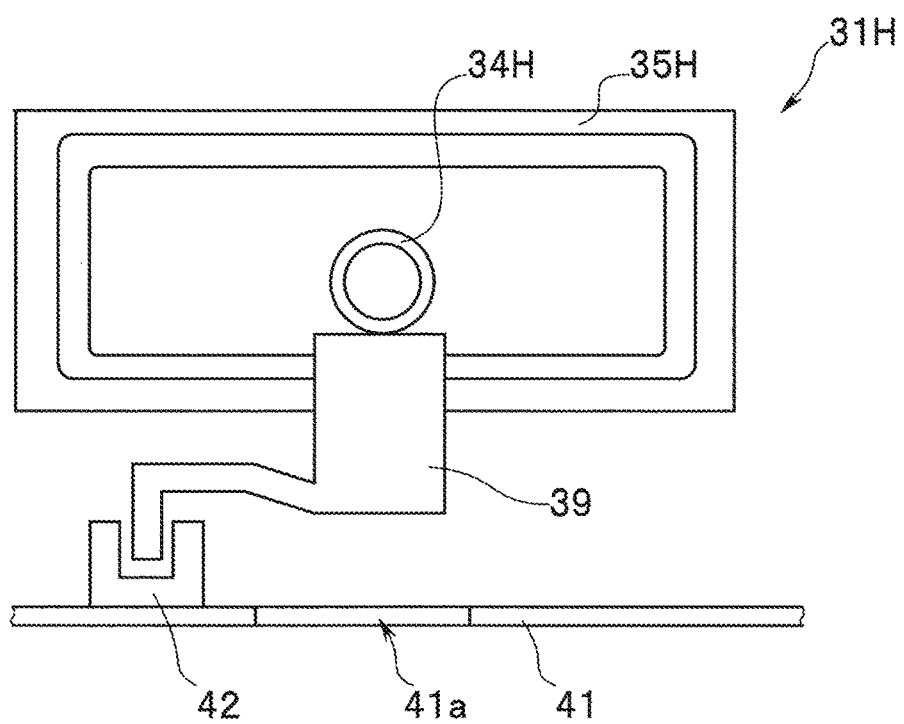
FIG. 19 is a plan view seen from a front of the receptacle in the connector apparatus in FIG. 18.
Figure 20:
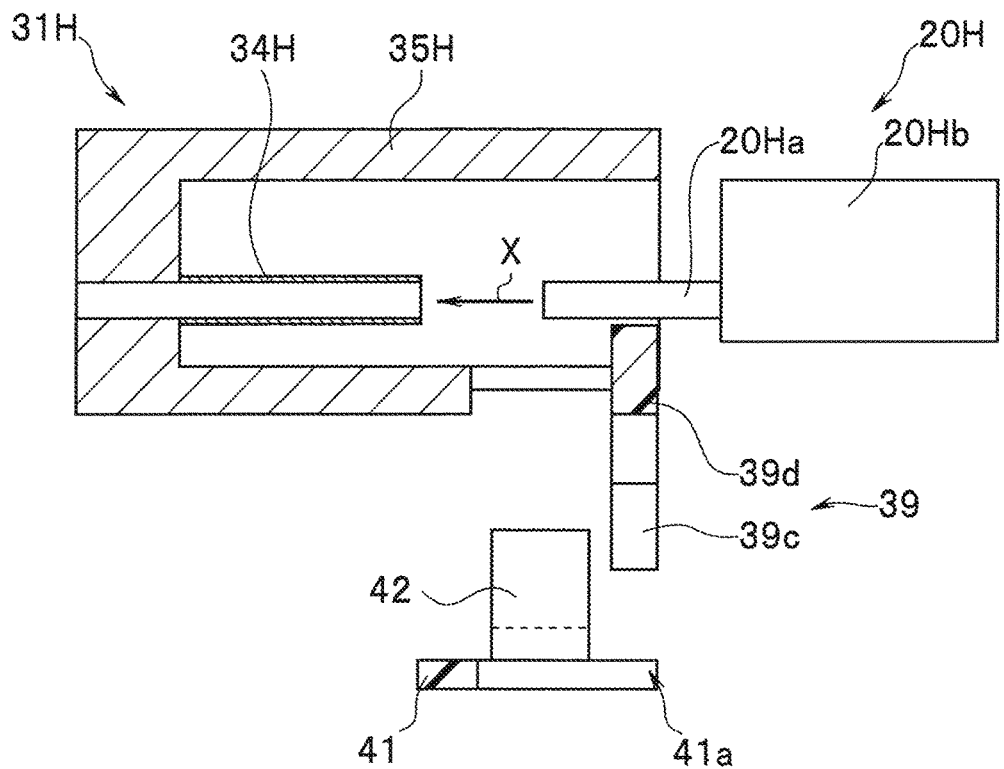
FIG. 20 is a conceptual diagram (side cross section) schematically illustrating an operation of the connector apparatus in FIG. 18.

FIG. 18 is an external perspective view schematically illustrating a configuration of the connector apparatus according to the second embodiment of the present invention. FIG. 19 is a plan view seen from a front of the receptacle in the connector apparatus in FIG. 18. FIG. 20 is a conceptual diagram schematically illustrating operation of the connector apparatus of the present embodiment. Note that FIG. 20 illustrates a side cross section of the connector apparatus.

The connector apparatus of the present embodiment includes the plug 20H and the receptacle 31H. Of these components, the plug 20H is constructed by including the plug body part 20H*b* having a substantially rectangular, cylindrical cross section as a whole and a substantially cylindrical plug shaft 20H*a*.

In correspondence with this, the receptacle 31H is constructed by including a plug body receiving portion 35H having a rectangular, cylindrical cross section and a substantially cylindrical plug shaft insertion receiving portion 34H.

As schematically illustrated in FIG. 19 and FIG. 20, the receptacle 31H of the present embodiment is constructed by applying, as appropriate, the plug detection sensor unit (the moving member 39 and the sensor element 42) and the electric substrate 41 or the like, which are substantially the same as the corresponding components illustrated in the aforementioned first embodiment.

The connector apparatus of the present embodiment in such a configuration can also obtain effects similar to the effects of the aforementioned first embodiment.

The plug detection sensor unit illustrated in the above first to seventh modifications is similarly applicable to the configuration of the above second embodiment. In that case, exactly the same effects can be obtained for each of the modes.

[Third Embodiment]

A third embodiment, which will be described next, is exemplification of a case where the configuration of a plug detection sensor unit is different from the configurations in the aforementioned first and second embodiments (and respective modifications).

The moving member configured to move in conjunction with an insertion operation of the plug into the receptacle according to the aforementioned first and second embodiments (and respective modifications) is configured to move in the same direction as the insertion direction of the plug.

By contrast, the moving member of the plug detection sensor unit according to the third embodiment of the present invention is configured to receive, when moving in conjunction with the insertion operation of the plug into the receptacle, a pushing pressure in the insertion direction of the plug, rotate around a predetermined axis of rotation and act on the sensor element.

Figure 21:
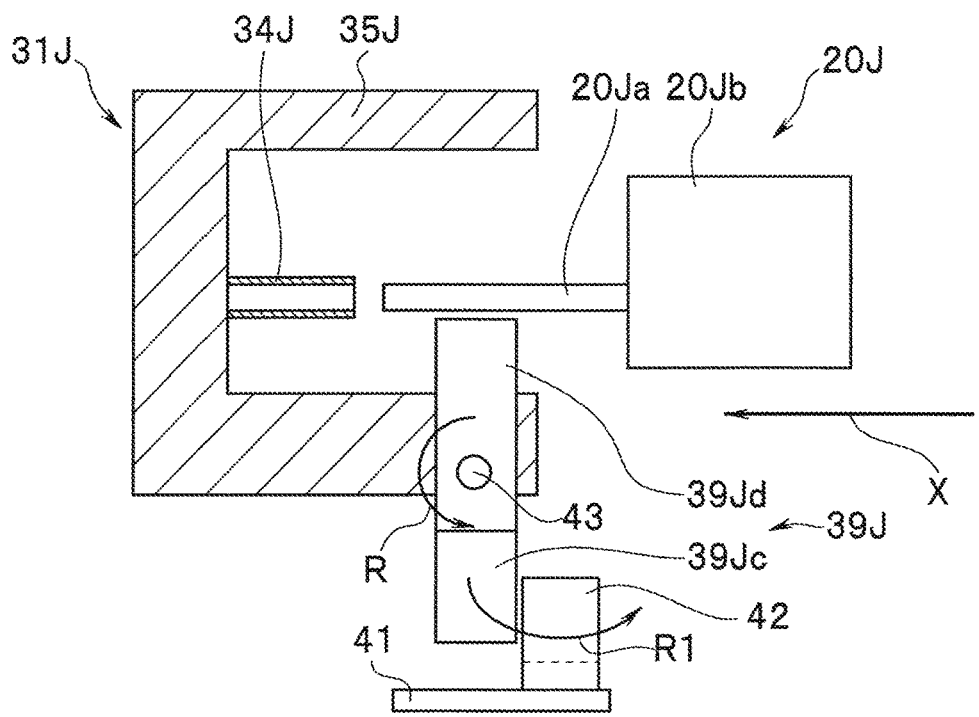
FIG. 21 is a conceptual diagram (side cross section) schematically illustrating a configuration of a connector apparatus according to a third embodiment of the present invention.
Figure 22:
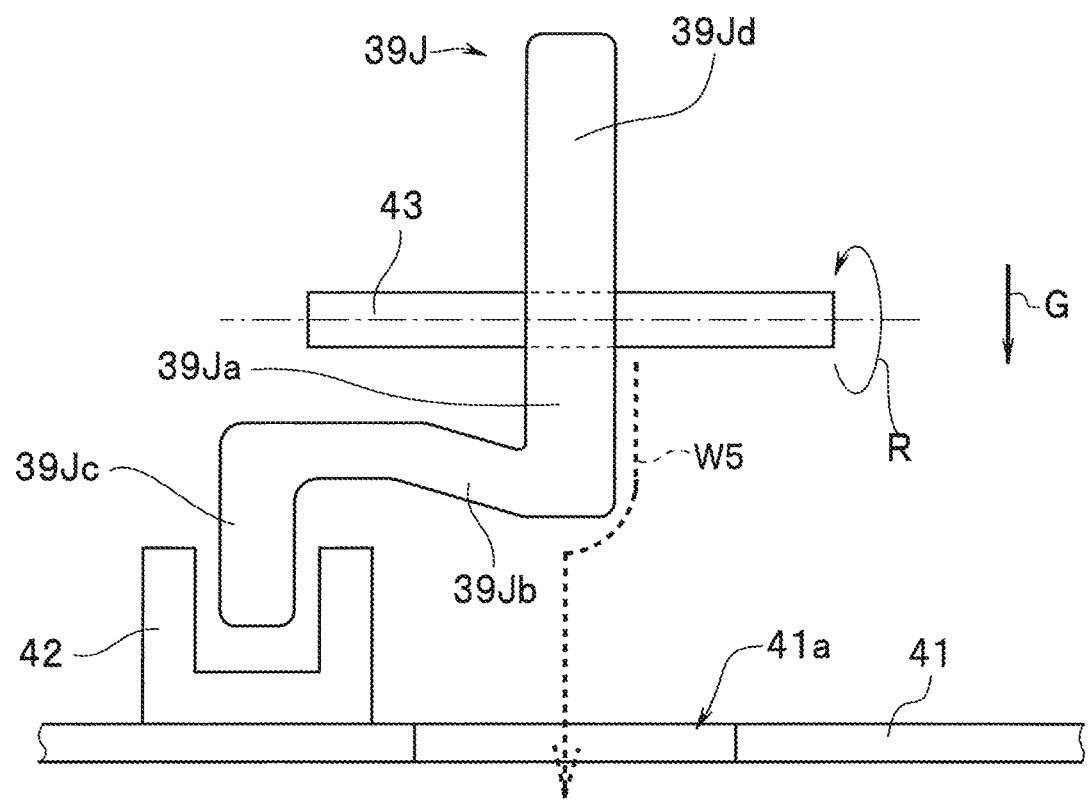
FIG. 22 is a conceptual diagram (plan seen from the front) schematically illustrating a plug detection sensor unit in the connector apparatus in FIG. 21.

FIG. 21 is a conceptual diagram schematically illustrating a configuration of the connector apparatus according to the third embodiment of the present invention. Note that FIG. 21 illustrates a side cross section of the connector apparatus. FIG. 22 is a conceptual diagram schematically illustrating a plug detection sensor unit of the connector apparatus of the present embodiment. Note that FIG. 22 illustrates a plan view seen from the front of the plug detection sensor unit.

The connector apparatus of the present embodiment includes a plug 20J and a receptacle 31J. Of these components, the plug 20J is constructed by including a substantially cylindrical plug shaft 20Ja and a plug body part 20Jb having a cylindrical shape as a whole. The configuration of the plug 20J is substantially the same as the configuration of the plug 20 described in the aforementioned first embodiment. Therefore, the illustration in FIG. 21 is simplified.

A basic configuration of the receptacle 31J is substantially the same as the configuration in the aforementioned first embodiment. In other words, the receptacle 31J is constructed by including a cylindrical plug body receiving portion 35J and a substantially cylindrical plug shaft insertion receiving portion 34J. In the present embodiment, the configuration of the plug detection sensor unit is different. Therefore, the illustration in FIG. 21 is also simplified.

The plug detection sensor unit of the present embodiment includes a moving member 39J and a sensor element 42. Of these components, the sensor element 42 is an electric part mounted on the electric substrate 41 of the connector apparatus and the same sensor element as the sensor element of the aforementioned first embodiment is applied.

The moving member 39J is formed by including a first portion 39Ja, a second portion 39Jb, a third portion 39Jc and a holding portion 39Jd as mainly shown in FIG. 22 and as in the case of the aforementioned first embodiment or the like. Here, configurations of the respective components are substantially the same as the configurations of the respective components in the first embodiment.

In other words, the first portion 39Ja is a region extending downward from the vicinity of a contact region with the receptacle 31J.

The second portion 39Jb is a region formed with one end connected to (one end of) the first portion 39Ja and the other end located above the one end.

The third portion 39Jc is a region formed with one end connected to (one end of) the second portion 39Jb and the other end extending downward. The third portion 39Jc moves in conjunction with the insertion of the plug 20J into the receptacle 31J. Thus, the third portion 39Jc acts on the sensor element 42. Therefore, the sensor element 42 detects the presence or absence of the plug 20J in the receptacle 31J (that is, whether the plug 20J is in a first state in which the plug 20J is located in the predetermined region in the receptacle 31J or the plug 20J is in a second state in which the plug 20J is not located in the predetermined region in the receptacle 31J).

The holding portion 39Jd is a region that can be movably held to a predetermined fixing portion of the receptacle body (not shown). The holding portion 39Jd is disposed at a predetermined position in the receptacle 31J such that part of the plug body part 20Jb comes into contact when the plug 20J is inserted into the receptacle 31J.

The moving member 39J configured in such a way is disposed so as to be rotatable with respect to the receptacle 31J around a rotation shaft 43.

The rotation shaft 43 is provided in an upright position with respect to the predetermined fixing portion of the receptacle body (not shown). In this case, the rotation shaft 43 is provided such that a longitudinal axis of the rotation shaft 43 is parallel to a direction along a line orthogonal to the horizontal direction with respect to the insertion direction (arrow X direction) of the plug 20J.

In this configuration, when the plug 20J is inserted into the receptacle 31J and the plug 20J moves in a predetermined direction (arrow X direction in FIG. 21), the moving member 39J is configured to rotate in a predetermined direction (arrow R direction in FIG. 21 and FIG. 22) in conjunction with the movement of the plug 20J.

When the moving member 39J rotates in the arrow R direction in FIG. 21 and FIG. 22 in conjunction with the movement of the plug 20J, the third portion 39Jc is configured to act on the sensor element 42 on the electric substrate 41 (see the arrow R1 in FIG. 21).

The electric substrate 41 is provided with the notch 41a as in the case of the aforementioned first embodiment. The notch 41a is disposed in a lower portion in the vicinity of the connection portion between the first portion 39Ja and the second portion 39Jb of the moving member 39J in the vertical direction G.

When a liquid infiltrating from outside flows downward from the holding portion 39d through the first portion 39Ja, this configuration allows the liquid to fall down from the vicinity of the connection portion between the first portion 39Ja and the second portion 39Jb as shown by a broken line arrow W5 in FIG. 22.

Since the notch 41a is disposed in the region below the vicinity of the connection portion between the first portion 39Ja and the second portion 39Jb in the vertical direction G, the dropping liquid is never attached to the electric substrate 41 or the sensor element 42.

The above third embodiment configured as described above can also obtain effects similar to the effects in the aforementioned first embodiment.

It goes without saying that the present invention is not limited to the above-described embodiments, but various modifications or applications can be made without departing from the gist and scope of the present invention. Furthermore, the above-described embodiments include inventions in various phases and various inventions can be extracted according to appropriate combinations in a plurality of disclosed configuration requirements. For example, even when some configuration requirements are deleted from all the configuration requirements shown in the embodiments, configurations from which these configuration requirements are deleted can be extracted as inventions when the problems to be solved by the invention can be solved and the effects described in the field of the effects of the invention can be achieved. Furthermore, components corresponding to different embodiments may be combined as appropriate. The present invention is not restricted by any specific embodiment except being limited by the attached claims.

What is claimed is:

1. A connector apparatus comprising:
    a receptacle into which a plug provided at a terminal end of a cable is inserted, the receptacle being provided in a device to which the plug is connected;
    a moving member in contact with the receptacle and configured to move in conjunction with insertion of the plug into the receptacle; and
    a sensor provided below the receptacle and configured to detect presence or absence of the plug in a predetermined region in the receptacle, wherein
    the moving member comprises:
    a first portion extending downward from a vicinity of a contact region with the receptacle;
    a second portion, one end of the second portion is connected to the first portion and another end of the second portion is located above the one end; and
    a third portion, one end of the third portion is connected to the second portion and configured to move in conjunction with the insertion of the plug into the receptacle to thereby switch between a first state in which the plug is disposed in the predetermined region and a second state in which the plug is not disposed in the predetermined region according to the detection by the sensor.

2. The connector apparatus according to claim 1, wherein the third portion is formed with another end extending downward, and
the other end of the third portion switches between the first state and the second state according to the detection by the sensor.

3. The connector apparatus according to claim 1, wherein the sensor is not disposed in a region below the first portion in a vertical direction, but disposed in any region other than the region below the first portion in the vertical direction.

4. The connector apparatus according to claim 1, wherein the moving member further comprises a fourth portion extending downward from a vicinity of a connection portion between the first portion and the second portion in the vertical direction.

5. The connector apparatus according to claim 1, wherein the moving member further comprises a through hole penetrating downward in the vertical direction in a vicinity of a connection portion between the first portion and the second portion.

6. The connector apparatus according to claim 1, wherein a side face of the moving member in a vicinity of at least a connection portion between the first portion and the second portion is formed in an R shape.

7. The connector apparatus according to claim 1, wherein the moving member further comprises a fifth portion, one end of the fifth portion is connected in a vicinity of a connection portion between the first portion and the second portion, and another end of the fifth portion extends so as to be located at a position lower than the connection portion between the first portion and the second portion.

8. The connector apparatus according to claim 1, further comprising an electric substrate provided at a position lower than the receptacle, on which the sensor is disposed, wherein the electric substrate is not disposed in a region below the first portion in the vertical direction but disposed in any region other than the region below the first portion in the vertical direction.

9. The connector apparatus according to claim 8, wherein the electric substrate is formed by including a notch in the region below the first portion in the vertical direction.

10. The connector apparatus according to claim 1, wherein
the sensor is provided in plurality, and
the moving member comprises the third portion formed in plurality.

11. The connector apparatus according to claim 10, wherein the sensor in plurality and the third portion in plurality are disposed side by side in a horizontal direction across the first portion.

12. The connector apparatus according to claim 10, wherein
the sensor in plurality and the third portion in plurality are disposed side by side along an insertion direction of the plug.

13. The connector apparatus according to claim 12, wherein the sensor in plurality and the third portion in plurality are disposed side by side at equal intervals.

14. The connector apparatus according to claim 12, wherein the sensor in plurality and the third portion in plurality are disposed side by side at different intervals.

15. The connector apparatus according to claim 10, wherein the sensor in plurality and the third portion in plurality are disposed side by side in a horizontal direction with respect to an insertion direction of the plug.

16. The connector apparatus according to claim 15, wherein a position in the insertion direction of the plug of the one of the sensor in plurality and a position in the insertion direction of the plug of the other of the sensor in plurality are the same, and
a position in the insertion direction of the plug of the one of the third portion in plurality and a position in the insertion direction of the plug of the other of the third portion in plurality are the same.

17. The connector apparatus according to claim 15, wherein
a position in the insertion direction of the plug of the one of the sensor in plurality and a position in the insertion direction of the plug of the other of the sensor in plurality are different, and
a position in the insertion direction of the plug of the one of the third portion in plurality and a position in the insertion direction of the plug of the other of the third portion in plurality are different.

* * * * *